US012741942B2

(12) United States Patent
Inagaki et al.

(10) Patent No.: US 12,741,942 B2
(45) Date of Patent: Sep. 22, 2026

(54) SUBSTITUTED PYRIDAZINE COMPOUND

(71) Applicant: Tenvie Therapeutics, Inc., Brisbane, CA (US)

(72) Inventors: Yusuke Inagaki, Tokyo (JP); Takashi Kamikubo, Tokyo (JP); Takahiro Nigawara, Tokyo (JP); Junko Maeda, Tokyo (JP); Susumu Yamaki, Tokyo (JP); Ikumi Kuriwaki, Tokyo (JP); Maiko Iida, Tokyo (JP); Junichi Shishikura, Tokyo (JP); Yuka Koizumi, Tokyo (JP); Kenji Negoro, Tokyo (JP); Takanori Koike, Tokyo (JP); Kengo Saba, Tokyo (JP)

(73) Assignee: Tenvie Therapeutics, Inc., Brisbane, CA (US)

( * ) Notice: Subject to any disclaimer, the term of this patent is extended or adjusted under 35 U.S.C. 154(b) by 815 days.

(21) Appl. No.: 17/909,171

(22) PCT Filed: Mar. 26, 2021

(86) PCT No.: PCT/JP2021/012773

§ 371 (c)(1),
(2) Date: Sep. 2, 2022

(87) PCT Pub. No.: WO2021/193897

PCT Pub. Date: Sep. 30, 2021

(65) Prior Publication Data

US 2023/0107277 A1 Apr. 6, 2023

(30) Foreign Application Priority Data

Mar. 27, 2020 (JP) ................................ 2020-057623

(51) Int. Cl.
*C07D 237/20* (2006.01)
*A61P 25/28* (2006.01)
*A61P 29/00* (2006.01)

(52) U.S. Cl.
CPC ............ *C07D 237/20* (2013.01); *A61P 25/28* (2018.01); *A61P 29/00* (2018.01)

(58) Field of Classification Search
CPC .................................................... C07D 237/20
See application file for complete search history.

(56) References Cited

U.S. PATENT DOCUMENTS

| | | | |
|---|---|---|---|
| 4,353,903 | A | 10/1982 | Fabiani et al. |
| 6,602,872 | B1 | 8/2003 | McIntyre et al. |
| 6,664,256 | B1 | 12/2003 | Ohkuchi et al. |
| 2012/0157410 | A1 | 6/2012 | Watterson et al. |

FOREIGN PATENT DOCUMENTS

| | | | |
|---|---|---|---|
| EP | 0429344 | A1 | 5/1991 |
| EP | 0429344 | B1 | 9/1996 |
| EP | 1300399 | A1 | 4/2003 |
| JP | 2003-517477 | A | 5/2003 |
| WO | 2001/042241 | A1 | 6/2001 |
| WO | 2002/004427 | A1 | 1/2002 |
| WO | 2017/184604 | A1 | 10/2017 |
| WO | 2018/015445 | A1 | 1/2018 |
| WO | 2019/008025 | A1 | 1/2019 |
| WO | 2020/234715 | A1 | 11/2020 |
| WO | 2022/135567 | A1 | 6/2022 |

OTHER PUBLICATIONS

American Chemical Society. Chemical Abstract Service. 1984. (Year: 1984).*
International Search Report for Application No. PCT/JP2021/012773, dated Jun. 1, 2021, 2 pages.
Wermuth et al., SR 46559 A and related aminopyridazines are potent muscarinic agonists with No. cholinergic syndrome. Bioorganic & Medicinal Chemistry Letters. Aug. 1992;2(8): 833-838.
European Office Action for Application No. 21775125.4, dated Apr. 22, 2024, 8 pages.

* cited by examiner

*Primary Examiner* — John S Kenyon
(74) *Attorney, Agent, or Firm* — McCarter & English, LLP; Wei Song; James M. Alburger

(57) ABSTRACT

The object of the present invention is to provide a pharmaceutical composition, in particular, a compound suitable for prevention and/or treatment of an inflammatory disease and/or a neurodegenerative disease. The present inventors have extensively conducted studies for discovering a compound having an inhibitory action on NLRP3 inflammasome activation, and found that substituted pyridazine compound has an inhibitory action on NLRP3 inflammasome activation. In this way, the present invention has been attained. The substituted pyridazine compound of the present invention is expected to serve as a prophylactic and/or therapeutic drug for an inflammatory disease and/or a neurodegenerative disease.

16 Claims, 2 Drawing Sheets

## P<0.01, Student's t-test
** P<0.01, Dunnett's multiple comparison test
N=10, mean value ± SEM

## P<0.01, Student's t-test
*P<0.05, **P<0.01, Dunnett's multiple comparison test
N=14-16, mean value ± SEM N=6, mean value ± SEM

SUBSTITUTED PYRIDAZINE COMPOUND

CROSS-REFERENCE TO RELATED APPLICATIONS

This application is a 35 U.S.C. § 371 national stage filing of International Application No. PCT/JP2021/012773 filed on Mar. 26, 2021, which in turn claims the benefit of Japanese Patent Application No. 2020-057623, filed on Mar. 27, 2020.

TECHNICAL FIELD

The present invention relates to a substituted pyridazine compound or a salt thereof which has an inhibitory action on NLRP3 inflammasome activation, and is expected to be useful as an active ingredient of a pharmaceutical composition, for example a pharmaceutical composition for prevention and/or treatment of an inflammatory disease or a neurodegenerative disease.

BACKGROUND ART

Inflammasome, which is excited by endogenous and exogenous alarm molecules, is a protein assembly inside the cell. Inflammasome is an organization which amplifies inflammatory response by activation due to cleavage of inflammatory cytokines IL-1β and IL-18 and induction of cell death through activation of caspase 1. A plurality of types of recognition molecule for alarm molecules are known, including NLRP1, NLRP3, NLRC4 and AIM2, and NLRP3 is activated by recognizing cellular stress from ATP molecules and pathogen toxins outside the cell, crystals of uric acid and cholesterol, abnormal aggregates of proteins, and the like.

As a disease caused by the gain-of-function mutation of NLRP3, cryopyrin-associated periodic syndrome (CAPS) is known (Nature Genetics, Vol. 29, No. 3, p. 301-305, 2001). NLRP3 inflammasome has been reported to be activated or expressed at a high level in a wide variety of diseases such as gout (Arthritis research and Therapy, Vol. 12, No. 2, Article No. 206, 2010), non-alcoholic steatohepatitis (Journal of Molecular Medicine, Vol. 92, No. 10, p. 1069-1082, 2014), inflammatory bowel disease (Cut, Vol. 59, No. 9, p. 1192-1100, 2010), Alzheimer's disease (Nature, Vol. 493, No. 7434, p. 674-678, 2013), Parkinson's disease (PloS ONE, Vol. 8, No. 1, Article No. e55375, 2013), amyotrophic lateral sclerosis (Inflammation, Vol. 41, No. 1, p. 93-103, 2018) and multiple system atrophy (Journal of Neuropathology and Experimental Neurology, Vol. 77, No. 11, p. 1055-1065, 2018).

Patent Literature 1 discloses that a compound represented by the following formula has an inhibitory action on NLRP3 inflammasome activation, and is useful as a therapeutic drug for various inflammatory diseases including CAPS (for the symbols in the formula, see the publication concerned).

[Formula 1]

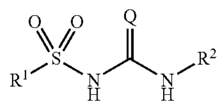

Patent Literature 2 discloses that a compound represented by the following formula has an inhibitory action on NLRP3 inflammasome activation, and is useful as a therapeutic drug for various inflammatory diseases including CAPS (for the symbols in the formula, see the publication concerned).

[Formula 2]

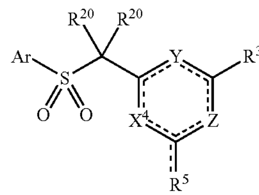

Patent Literature 3 discloses that a compound represented by the following formula has an inhibitory action on NLRP3 inflammasome activation, and is useful as a therapeutic drug for various inflammatory diseases including CAPS (for the symbols in the formula, see the publication concerned).

[Formula 3]

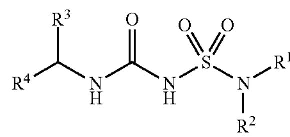

Patent Literature 4, which was published after the priority date of the present application, discloses that a compound represented by the following formula has an inhibitory action on NLRP3 inflammasome activation, and is useful as a therapeutic drug for various inflammatory diseases including CAPS (for the symbols in the formula, see the publication concerned).

[Formula 4]

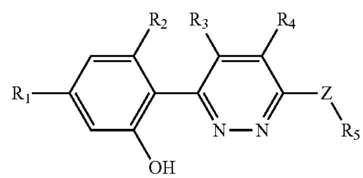

CITATION LIST

Patent Literature

PTL 1: International Publication No. WO 2019/008025
PTL 2: International Publication No. WO 2017/184604
PTL 3: International Publication No. WO 2018/015445
PTL 4: International Publication No. WO 2020/234715

SUMMARY OF INVENTION

Technical Problem

There is provided a compound which has an inhibitory action on NLRP3 inflammasome activation, and is expected to be useful as an active ingredient of a pharmaceutical composition, particularly a pharmaceutical composition for prevention and/or treatment of an inflammatory disease, a neurodegenerative disease or the like.

Solution to Problem

The present inventors have extensively conducted studies on a compound having an inhibitory action on NLRP3 inflammasome activation, and as a result, have found that a substituted pyridazine compound has an inhibitory action on NLRP3 inflammasome activation, and is expected to be useful as an active ingredient of a pharmaceutical composition for prevention and/or treatment of an inflammatory disease, a neurodegenerative disease or the like, particularly α-synucleinopathies and multiple sclerosis. In this way, the present invention has been attained.

Specifically, the present invention relates to a compound of formula (I) or a salt thereof, and a pharmaceutical composition comprising a compound of formula (I) or a salt thereof and one or more pharmaceutically acceptable excipients.

[Formula 5]

(I)

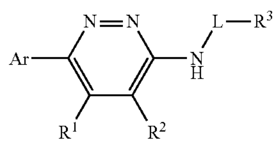

wherein

Ar is a group represented by the following formula (i) or (ii):

[Formula 6]

(i)

(ii)

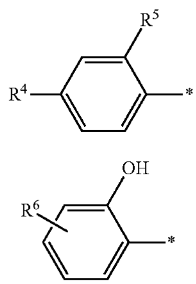

wherein * represents a bonding site to the pyridazine ring of formula (I);

L is $C_{1-6}$ alkylene or $C_{3-8}$ cycloalkylene;

$R^1$ is H, $C_{1-6}$ alkyl, $C_{3-8}$ cycloalkyl, aryl, heteroaryl optionally substituted with 1 to 4 $C_{1-6}$ alkyls, cyano, —$OR^7$ or —$N(C_{1-6}$ alkyl$)_2$;

$R^2$ is H, $C_{1-6}$ alkyl, $C_{3-8}$ cycloalkyl, aryl, heteroaryl optionally substituted with 1 to 4 $C_{1-6}$ alkyls, cyano, —$OR^7$, —$N(C_{1-6}$ alkyl$)_2$, —C(═O)O—$C_{1-6}$ alkyl or —C(═O)$NR^8R^9$;

$R^3$ is OH, —NHC(═O)$R^{10}$ or —OC(═O)—$C_{1-6}$ alkyl;

$R^4$ is halogen, —O—$C_{1-6}$ alkyl or halogeno $C_{1-6}$ alkyl;

$R^5$ is H, $C_{3-8}$ cycloalkyl or halogeno $C_{1-6}$ alkyl;

$R^6$ is H, halogen, —O—$C_{1-6}$ alkyl or halogeno $C_{1-6}$ alkyl;

$R^7$ is —$C_{1-6}$ alkylene-O—$C_{1-6}$ alkylene-aryl or halogeno $C_{1-6}$ alkyl;

$R^8$ and $R^9$ are the same or different, and each are H or $C_{1-6}$ alkyl; or $R^8$ and $R^9$, together with a nitrogen atom to which $R^8$ and $R^9$ are bonded, form morpholine, piperazine or thiomorpholine and the morpholine, piperazine or thiomorpholine is optionally substituted with $C_{1-6}$ alkyl; and $R^{10}$ is $C_{1-6}$ alkyl, halogeno $C_{1-6}$ alkyl or $C_{3-8}$ cycloalkyl, provided that when Ar is a group represented by formula (i) with $R^5$ being H, $R^4$ is halogeno $C_{1-6}$ alkyl, and one of $R^1$ and $R^2$ is a group other than H.

When symbols in a chemical formula are used in other chemical formulae herein, the same symbols represent the same meanings unless otherwise specified.

The present invention also relates to a pharmaceutical composition for prevention and/or treatment of an inflammatory disease or a neurodegenerative disease, the pharmaceutical composition comprising a compound of formula (I) or a salt thereof and a pharmaceutically acceptable excipient. The pharmaceutical composition encompasses a preventive and/or therapeutic agent for an inflammatory disease or a neurodegenerative disease, the agent comprising a compound of formula (I) or a salt thereof.

The present invention also relates to a compound of formula (I) or a salt thereof which is an NLRP3 inflammasome activation inhibitor; a compound of formula (I) or a salt thereof for use as an NLRP3 inflammasome activation inhibitor; an NLRP3 inflammasome activation inhibitor comprising a compound of formula (I) or a salt thereof; use of a compound of formula (I) or a salt thereof for producing a pharmaceutical composition for prevention and/or treatment of an inflammatory disease and/or a neurodegenerative disease; use of a compound of formula (I) or a salt thereof for prevention and/or treatment of an inflammatory disease and/or a neurodegenerative disease; a compound of formula (I) or a salt thereof for use in prevention and/or treatment of an inflammatory disease and/or a neurodegenerative disease; and a method for preventing and/or treating an inflammatory disease and/or a neurodegenerative disease, the method comprising administering an effective amount of a compound of formula (I) or a salt thereof to a subject.

The "subject" is a human or another animal that needs prevention or treatment of the disease. In an embodiment, the "subject" is a human that needs prevention or treatment of the disease.

Advantageous Effects of Invention

A compound of formula (I) or a salt thereof has an inhibitory action on NLRP3 inflammasome activation, and can be used as a prophylactic or therapeutic drug for an inflammatory disease and/or a neurodegenerative disease etc.

DESCRIPTION OF EMBODIMENTS

Figure 1:
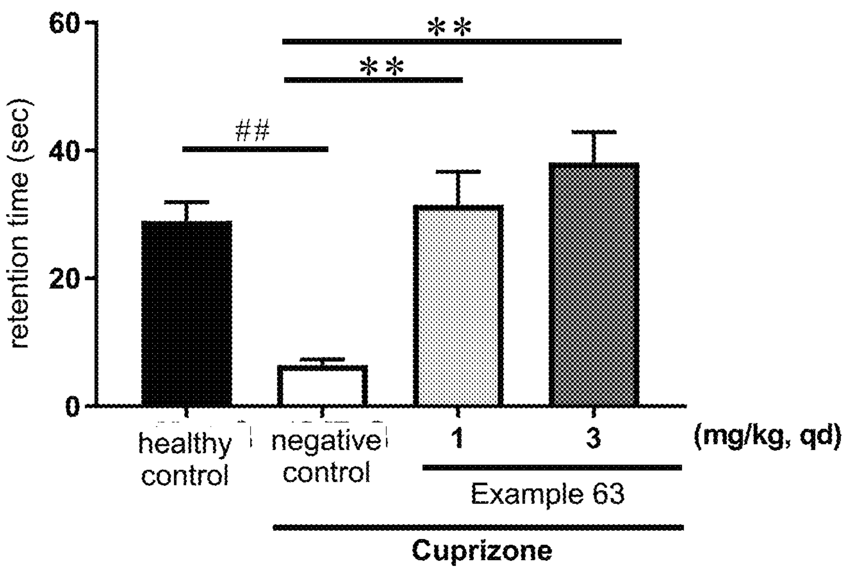
FIG. 1 shows results of the hanging wire test which evaluates an improving effect of the compound of the Example 63 to a movement disorder in Cuprizone-induced neuroinflammation model.

Hereinafter, the present invention will be described in detail.

Herein, the following terms have the meanings given below unless otherwise specified. The following definitions are intended to clarify the defined terms rather than imposing limitations. When terms used herein are not specifically defined, the terms are used to intend meanings that are generally accepted by those skilled in the art.

Herein, the "$C_{1-6}$ alkyl" is a linear or branched alkyl group having 1 to 6 carbon atoms (hereinafter, abbreviated as $C_{1-6}$), for example methyl, ethyl, n-propyl, isopropyl, n-butyl, isobutyl, sec-butyl, tert-butyl, n-pentyl, n-hexyl or the like. The "$C_{1-6}$ alkyl" is a linear or branched $C_{1-4}$ alkyl in an embodiment; methyl, ethyl, n-propyl, isopropyl or n-butyl in another embodiment; methyl in yet another embodiment; or n-propyl in still another embodiment.

The "$C_{3-8}$ cycloalkyl" is a $C_{3-8}$ saturated hydrocarbon ring group, and may have a cross-linkage or form a spiro ring. The "$C_{3-8}$ cycloalkyl" is, for example, cyclopropyl, cyclobutyl, cyclopentyl, cyclohexyl, cycloheptyl, cyclooctyl, bicyclo[2.2.1]heptyl, bicyclo[3.1.0]hexyl, bicyclo[3.1.1]heptyl or spiro[2.5]octyl. The cycloalkyl is cyclopropyl, cyclobutyl, cyclopentyl, cyclohexyl, cycloheptyl or cyclooctyl in an embodiment; cyclopropyl, cyclobutyl, cyclopentyl or cyclohexyl in another embodiment; cyclopropyl in yet another embodiment; or cyclohexyl in still another embodiment.

The "$C_{3-8}$ cycloalkylene" is a divalent group in which two carbon atoms forming the ring have a bonding hand, among the above-described "$C_{3-8}$ cycloalkyls". Specifically, the "$C_{3-8}$ cycloalkylene" is, for example, cyclopropanediyl, cyclobutanediyl, cyclopentadiyl, cyclohexanediyl, cycloheptanediyl or cyclooctanediyl; or cyclohexanediyl in an embodiment.

The "aryl" is a $C_{6-14}$ monocyclic to tricyclic aromatic hydrocarbon ring group, and encompasses ring groups formed by fusion with a $C_{5-8}$ cycloalkene at a double bond site thereof. The "aryl" is, for example, phenyl, naphthyl, 5-tetrahydronaphthyl, 4-indenyl, 1-fluorenyl or the like; or phenyl in an embodiment.

The "heteroaryl" is a 5- to 6-membered aromatic ring group having 1 to 4 hetero atoms selected from oxygen, sulfur and nitrogen, and examples thereof include pyrrolyl, furyl, thienyl, pyrazolyl, imidazolyl, isoxazolyl, oxazolyl, isothiazolyl, thiazolyl, triazolyl, oxadiazolyl, thiadiazolyl, tetrazolyl, pyridyl, pyrazinyl, pyrimidinyl, pyridazinyl and triazinyl. The "heteroaryl" is furyl, imidazolyl or pyrazolyl in an embodiment; or pyrazolyl in another embodiment.

The "halogen" means F, Cl, Br or I. The "halogen" is F or Cl in an embodiment; F in another embodiment; or Cl in yet another embodiment.

The "halogeno $C_{1-6}$ alkyl" is a linear or branched $C_{1-6}$ alkyl group substituted with one or more halogens. The "halogeno $C_{1-6}$ alkyl" is trifluoromethyl, trifluoroethyl, trifluoropropyl, 2-fluoro-2-methylpropyl, difluoromethyl, fluoromethyl or chloromethyl in an embodiment; trifluoromethyl in another embodiment; or difluoromethyl in yet another embodiment.

The "$C_{1-6}$ alkylene" is a linear or branched $C_{1-6}$ alkylene, for example, methylene, ethylene, trimethylene, tetramethylene, pentamethylene, hexamethylene, methylmethylene, propylene, 2-methyltrimethylene, ethylethylene, 1,2-dimethylethylene or 1,1,2,2-tetramethylethylene. The "$C_{1-6}$ alkylene" is $C_{1-4}$ alkylene in an embodiment; or methylene, ethylene or propylene in another embodiment; or propylene in yet another embodiment.

In the expression "when Ar is a group represented by formula (i) with $R^5$ being H, $R^4$ is halogeno $C_{1-6}$ alkyl, and one of IV and $R^2$ is a group other than H", the "group other than H" is $C_{1-6}$ alkyl, aryl or heteroaryl in an embodiment; or methyl, phenyl or furyl in another embodiment.

The term "optionally substituted" herein means that a group is unsubstituted or "substituted with one or more substituents". The group of interest may be substituted at any position at which hydrogen is originally present in the group.

One or more embodiments may be combined with another embodiment even if the combination is not specifically described.

The "inflammatory disease" herein refers to autoinflammatory diseases including cryopyrin-associated periodic syndrome (CAPS) including a disease group consisting of familial cold autoinflammatory syndrome (FCAS), Muckle-Wells syndrome (MWS) and neonatal onset multisystem inflammatory disease/chronic infantile neurologic cutaneous and articular syndrome (NOMID/CINCA), gout and pseudogout; and diseases including non-alcoholic steatohepatitis (NASH), but the "inflammatory disease" is not limited to these diseases. The "inflammatory disease" is an autoinflammatory disease in an embodiment; or CAPS in another embodiment.

The "neurodegenerative disease" herein refers to a disease group including α-synucleinopathies including Parkinson's disease, multiple system atrophy and Lewy body dementia; Alzheimer's disease; amyotrophic lateral sclerosis; and multiple sclerosis, but the "neurodegenerative disease" is not limited to these diseases. The "neurodegenerative disease" is Alzheimer's disease, multiple sclerosis or amyotrophic lateral sclerosis in an embodiment; α-synucleinopathies in another embodiment; or multiple system atrophy in still another embodiment; or α-synucleinopathies or multiple sclerosis in yet another embodiment.

Some embodiments of the compound of formula (I) or salt thereof in the present invention will be shown below.

(1-1) A compound or a salt thereof in which Ar is a group represented by the following formula (i) or formula (ii):

[Formula 7]

(i)

(ii)

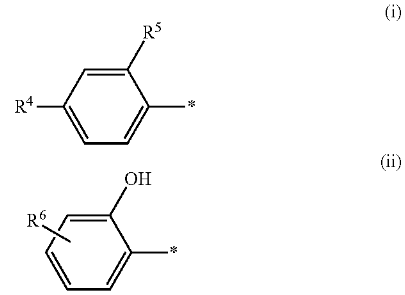

wherein $R^4$ is halogen, —O—$C_{1-6}$ alkyl or halogeno $C_{1-6}$ alkyl, $R_5$ is H, $C_{3-8}$ cycloalkyl or halogeno $C_{1-6}$ alkyl, and $R^6$ is H, halogen, —O—$C_{1-6}$ alkyl or halogeno $C_{1-6}$ alkyl, provided that when Ar is a group represented by formula (i) with $R^5$ being H, $R^4$ is halogeno $C_{1-6}$ alkyl and one of $R^1$ and $R^2$ is a group other than H.

(1-2) A compound or a salt thereof in which Ar is a group represented by formula (i) or formula (ii), wherein $R^4$ is halogen, —O—$C_{1-6}$ alkyl or halogeno $C_{1-6}$ alkyl, $R_5$ is $C_{3-8}$ cycloalkyl or halogeno $C_{1-6}$ alkyl, and $R^6$ is H, halogen, —O—$C_{1-6}$ alkyl or halogeno $C_{1-6}$ alkyl.

(1-3) A compound or a salt thereof in which Ar is a group represented by formula (i), wherein $R^4$ is halogen, —O—$C_{1-6}$ alkyl or halogeno $C_{1-6}$ alkyl, and $R_5$ is $C_{3-8}$ cycloalkyl or halogeno $C_{1-6}$ alkyl.

(1-4) A compound or a salt thereof in which Ar is a group represented by formula (i), wherein each of $R^4$ and $R^5$ is halogeno $C_{1-6}$ alkyl.

(1-5) A compound or a salt thereof in which Ar is a group represented by formula (ii), wherein $R^6$ is H, halogen, —O—$C_{1-6}$ alkyl or halogeno $C_{1-6}$ alkyl.

(1-6) A compound or a salt thereof in which Ar is a group represented by formula (ii), wherein $R^6$ is halogeno $C_{1-6}$ alkyl.

(2-1) A compound or a salt thereof in which L is $C_{1-6}$ alkylene or $C_{3-8}$ cycloalkylene.

(2-2) A compound or a salt thereof in which L is $C_{1-6}$ alkylene.

(2-3) A compound or a salt thereof in which L is $C_{3-8}$ cycloalkylene.

(3-1) A compound or a salt thereof in which $R^1$ is H, $C_{1-6}$ alkyl, $C_{3-8}$ cycloalkyl, aryl, heteroaryl optionally substituted with 1 to 4 $C_{1-6}$ alkyls, cyano, —$OR^7$ or —N($C_{1-6}$ alkyl)$_2$, wherein $R^7$ is —$C_{1-6}$ alkylene-O—$C_{1-6}$ alkylene-aryl or halogeno $C_{1-6}$ alkyl.

(3-2) A compound or a salt thereof in which R' is H, $C_{1-6}$ alkyl or $C_{3-8}$ cycloalkyl.

(3-3) A compound or a salt thereof in which R' is H or $C_{1-6}$ alkyl.

(3-4) A compound or a salt thereof in which R' is H.

(3-5) A compound or a salt thereof in which R' is $C_{1-6}$ alkyl.

(3-6) A compound or a salt thereof in which R' is $C_{1-6}$ alkyl, $C_{3-8}$ cycloalkyl, aryl, heteroaryl optionally substituted with 1 to 4 $C_{1-6}$ alkyls, cyano, —$OR^7$ or —N($C_{1-6}$ alkyl)$_2$, wherein $R^7$ is —$C_{1-6}$ alkylene-O—$C_{1-6}$ alkylene-aryl or halogeno $C_{1-6}$ alkyl.

(3-7) A compound or a salt thereof in which R' is $C_{1-6}$ alkyl or $C_{3-8}$ cycloalkyl.

(4-1) A compound or a salt thereof in which $R^2$ is H, $C_{1-6}$ alkyl, $C_{3-8}$ cycloalkyl, aryl, heteroaryl optionally substituted with 1 to 4 $C_{1-6}$ alkyls, cyano, —$OR^7$, —N($C_{1-6}$ alkyl)$_2$, —C(═O)O—$C_{1-6}$ alkyl or —C(═O)$NR^8R^9$, wherein $R^7$ is —$C_{1-6}$ alkylene-O—$C_{1-6}$ alkylene-aryl or halogeno $C_{1-6}$ alkyl;

$R^8$ and $R^9$ are the same or different, and each are H or $C_{1-6}$ alkyl; or $R^8$ and $R^9$, together with a nitrogen atom to which $R^8$ and $R^9$ are bonded, form morpholine, piperazine or thiomorpholine, and the morpholine, piperazine or thiomorpholine is optionally substituted with $C_{1-6}$ alkyl.

(4-2) A compound or a salt thereof in which $R^2$ is H, $C_{1-6}$ alkyl, $C_{3-8}$ cycloalkyl or cyano.

(4-3) A compound or a salt thereof in which $R^2$ is H or $C_{1-6}$ alkyl.

(4-4) A compound or a salt thereof in which $R^2$ is H.

(4-5) A compound or a salt thereof in which $R^2$ is $C_{1-6}$ alkyl.

(5-1) A compound or a salt thereof in which $R^3$ is OH, —NHC(═O)$R^{10}$ or —OC(═O)—$C_{1-6}$ alkyl, wherein $R^{10}$ is $C_{1-6}$ alkyl, halogeno $C_{1-6}$ alkyl or $C_{3-8}$ cycloalkyl.

(5-2) A compound or a salt thereof in which $R^3$ is OH.

(6) Compounds or salts thereof which are combinations of two or more embodiments that are not mutually contradictory, among the embodiments of the groups described in (1-1) to (5-2). Examples thereof include, but are not limited to, the following combinations.

(6-1) A compound or a salt thereof which is a combination of the embodiments of (1-1), (2-1), (3-1), (4-1) and (5-1).

(6-2) A compound or a salt thereof which is a combination of the embodiments of (1-2), (2-1), (3-1), (4-1) and (5-1).

(6-3) A compound or a salt thereof which is a combination of the embodiments of (1-2), (2-1), (3-1), (4-1) and (5-2).

(6-4) A compound or a salt thereof which is a combination of the embodiments of (1-2), (2-1), (3-2), (4-2) and (5-2).

(6-5) A compound or a salt thereof which is a combination of the embodiments of (1-2), (2-1), (3-3), (4-3) and (5-2).

(6-6) A compound or a salt thereof which is a combination of the embodiments of (1-3), (2-1), (3-2), (4-2) and (5-2).

(6-7) A compound or a salt thereof which is a combination of the embodiments of (1-3), (2-1), (3-3), (4-3) and (5-2).

(6-8) A compound or a salt thereof which is a combination of the embodiments of (1-4), (2-1), (3-3), (4-3) and (5-2).

(6-9) A compound or a salt thereof which is a combination of the embodiments of (1-4), (2-2), (3-5), (4-4) and (5-2).

(6-10) A compound or a salt thereof which is a combination of the embodiments of (1-4), (2-2), (3-4), (4-5) and (5-2).

(6-11) A compound or a salt thereof which is a combination of the embodiments of (1-4), (2-2), (3-5), (4-5) and (5-2).

(6-12) A compound or a salt thereof which is a combination of the embodiments of (1-4), (2-3), (3-5), (4-4) and (5-2).

(6-13) A compound or a salt thereof which is a combination of the embodiments of (1-4), (2-3), (3-4), (4-5) and (5-2).

(6-14) A compound or a salt thereof which is a combination of the embodiments of (1-4), (2-3), (3-5), (4-5) and (5-2).

(6-15) A compound or a salt thereof which is a combination of the embodiments of (1-5), (2-1), (3-2), (4-2) and (5-2).

(6-16) A compound or a salt thereof which is a combination of the embodiments of (1-5), (2-1), (3-3), (4-3) and (5-2).

(6-17) A compound or a salt thereof which is a combination of the embodiments of (1-6), (2-1), (3-3), (4-3) and (5-2).

(6-18) A compound or a salt thereof which is a combination of the embodiments of (1-6), (2-2), (3-5), (4-4) and (5-2).

(6-19) A compound or a salt thereof which is a combination of the embodiments of (1-6), (2-2), (3-4), (4-5) and (5-2).

(6-20) A compound or a salt thereof which is a combination of the embodiments of (1-6), (2-2), (3-5), (4-5) and (5-2).

(6-21) A compound or a salt thereof which is a combination of the embodiments of (1-6), (2-3), (3-5), (4-4) and (5-2).

(6-22) A compound or a salt thereof which is a combination of the embodiments of (1-6), (2-3), (3-4), (4-5) and (5-2).

(6-23) A compound or a salt thereof which is a combination of the embodiments of (1-6), (2-3), (3-5), (4-5) and (5-2).

Specific examples of the compounds encompassed in the present invention include the following compounds.

(2R)-1-({6-[2,4-bis(trifluoromethyl)phenyl]-4,5-dimethylpyridazin-3-yl}amino)propan-2-ol;

(2R)-1-({6-[2,4-bis(trifluoromethyl)phenyl]-5-methylpyridazin-3-yl}amino)propan-2-ol;

(2R)-1-({6-[2,4-bis(trifluoromethyl)phenyl]-4-methylpyridazin-3-yl}amino)propan-2-ol;

2-(6-{[(2R)-2-hydroxypropyl]amino}-4-methylpyridazin-3-yl)-5-(trifluoromethyl)phenol;

2-(6-{[(2R)-2-hydroxypropyl]amino}-5-methylpyridazin-3-yl)-5-(trifluoromethyl)phenol;

2-(6-{[(2R)-2-hydroxypropyl]amino}-4,5-dimethylpyridazin-3-yl)-5-(trifluoromethyl)phenol;

rac-(1R,2R)-2-({6-[2,4-bis(trifluoromethyl)phenyl]-5-methylpyridazin yl}amino)cyclohexan-1-ol;

rac-(1R,2R)-2-({6-[2,4-bis(trifluoromethyl)phenyl]-4-methylpyridazin yl}amino)cyclohexan-1-ol, 2-(6-{[(1R,2R)-2-hydroxycyclohexyl]amino}-4,5-dimethylpyridazin-3-yl) (trifluoromethyl)phenol; and 2-(6-{[(1R,2R)-2-hydroxycyclohexyl]amino}-4,5-dimethylpyridazine-3-yl) (trifluoromethyl)phenol monohydrochloride.

Further, examples of specific compounds included in the present invention include the following compounds or salts thereof.

(A) Crystals of 2-(6-{[(1R,2R)-2-hydroxycyclohexyl]amino}-4,5-dimethylpyridazine-3-yl)-5-(trifluoromethyl)phenol monohydrochloride.

(B) Crystals of 2-(6-{[(1R,2R)-2-hydroxycyclohexyl]amino}-4,5-dimethylpyridazine-3-yl)-5-(trifluoromethyl)phenol monohydrochloride, which are characterized in that the crystals have peaks near 20)(°=14.5, 16.3, 17.2, 18.4, 18.9, 22.1, 23.6, 24.9, 25.7 and 26.8 in powder X-ray diffraction using Cu as a tube.

(C) Crystals of 2-(6-{[(1R,2R)-2-hydroxycyclohexyl]amino}-4,5-dimethylpyridazine-3-yl)-5-(trifluoromethyl)phenol monohydrochloride, which are characterized in that the crystals have the onset temperature of the endothermic peak of around 227.32° C. in differential scanning calorimetry analysis (DSC analysis).

(D) Crystals of 2-(6-{[(1R,2R)-2-hydroxycyclohexyl]amino}-4,5-dimethylpyridazine-3-yl)-5-(trifluoromethyl)phenol monohydrochloride, which are characterized in that the crystals have the onset temperature of the endothermic peak of around 227.32° C. in differential scanning calorimetry analysis (DSC analysis) and peaks near 20)(°=14.5, 16.3, 17.2, 18.4, 18.9, 22.1, 23.6, 24.9, 25.7 and 26.8 in powder X-ray diffraction using Cu as a tube.

The present invention relates to: use of a compound of formula (I) or a salt thereof for producing a pharmaceutical composition for prevention and/or treatment of a neurodegenerative disease, particularly α-synucleinopathies or multiple sclerosis; use of a compound of formula (I) or a salt thereof for prevention and/or treatment of a neurodegenerative disease, particularly α-synucleinopathies or multiple sclerosis; a compound of formula (I) or a salt thereof for use in prevention and/or treatment of a neurodegenerative disease, particularly α-synucleinopathies or multiple sclerosis; and a method for preventing and/or treating a neurodegenerative disease, particularly α-synucleinopathies or multiple sclerosis, the method comprising administering an effective amount of a compound of formula (I) or a salt thereof to a subject.

The present invention also relates to a compound of formula (I) or a salt thereof, which shows an IL-1β production inhibitory effect in central nervous system of a subject.

In one embodiment of the present invention, the compound of the formula (I) or a salt thereof shows, for example, an IL-1β production inhibitory effect of 50% or more at a dose of 3 mg/kg or less in the measurement method of the Test Example 2. In another embodiment of the present invention, the compound of the formula (I) or a salt thereof shows, for example, an IL-1β production inhibitory effect of 50% or more at a dose of 1 mg/kg or less in the measurement method of the Test Example 2. In yet another embodiment of the present invention, the compound of the formula (I) or a salt thereof shows, for example, an IL-1β production inhibitory effect of 50% or more at a dose of 0.3 mg/kg or less in the measurement method of the Test Example 2.

Also, in an embodiment of the present invention, the compound of the formula (I) or a salt thereof is characterized by exhibiting no phototoxic effect. "No phototoxic effect" means that the phototoxicity is judged to be negative in the evaluation according to the method described in the OECD guideline for testing of chemicals 432: In vitro 3T3 NRU phototoxicity test, 2004.

Further, in an embodiment of the present invention, the compound of the formula (I) or a salt thereof is characterized in that the $IC_{50}$ value of the hERG inhibitory activity is 10 μM or more.

A compound of formula (I) can have tautomers or geometric isomers depending on the types of substituents. Herein, a compound of formula (I) or a salt thereof may be described as only one isomer form, but the present invention encompasses other isomers, and isolated isomers or mixtures thereof.

A compound of formula (I) or a salt thereof may have an asymmetric center or an axial chiral, and can have an enantiomer (optical isomer) due to the asymmetric center or the axial chiral. The compound of formula (I) or salt thereof encompasses all of individual isolated enantiomers such as an (R)-isomer and an (S)-isomer, and mixtures thereof (racemic mixtures or non-racemic mixtures). In an embodiment, the enantiomer is "stereochemically pure". The term "stereochemically pure" refers to a purity which allows a person skilled in the art to consider the isomer to be substantially stereochemically pure. In another embodiment, the enantiomer is a compound having a stereochemical purity of, for example, 90% ee (enantiomeric excess) or more, 95% ee or more, 98% ee or more or 99% ee or more.

Further, the present invention encompasses a pharmaceutically acceptable prodrugs of compounds represented by formula (I). The pharmaceutically acceptable prodrug is a compound having a group which can be converted into an amino group, a hydroxyl group, a carboxyl group or another group by solvolysis or under physiological conditions. Examples of the group for forming a prodrug include groups as described in Prog. Med., 5, 2157-2161 (1985) and "Pharmaceutical research and development" (Hirokawa-Shoten Ltd., 1990), Vol. 7, Molecular Design 163-198.

The salt of a compound of formula (I) is a pharmaceutically acceptable salt of the compound of formula (I), and may be an acid addition salt or a salt with a base depending on the type of a substituent. Specific examples thereof include acid addition salts with any of inorganic acids such as hydrochloric acid, hydrobromic acid, hydroiodic acid, sulfuric acid, nitric acid and phosphoric acid or any of organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid and glutamic acid; salts with any of inorganic bases such as sodium, potassium, magnesium, calcium and aluminum or any of organic bases such as methylamine, ethylamine, ethanolamine, lysin and ornithine; and salts with any of various amino acids such as acetylleucine and amino acid derivatives; and ammonium salts.

Further, the present invention encompasses various hydrates, solvates and crystal-polymorphic substances of the compound of formula (I) or salt thereof.

The present invention encompasses all of compounds of formula (I) or salts thereof labeled with one or more pharmaceutically acceptable radioactive or non-radioactive isotopes. Examples of preferred isotopes that are used for labeling the inventive compound with isotopes include isotopes of hydrogen (e.g. $^{2}H$ and $^{3}H$), carbon (e.g. $^{11}C$, $^{13}C$ and $^{14}C$), nitrogen (e.g. $^{13}N$ and $^{15}N$), oxygen (e.g. $^{15}O$, $^{17}O$ and $^{18}O$), fluorine (e.g. $^{18}F$), chlorine (e.g. $^{36}Cl$), iodine (e.g. $^{123}I$ and $^{125}I$), phosphorus (e.g. $^{32}P$) and sulfur (e.g. $^{35}S$). The isotopically labeled compound of the invention of the present application can be used for studies such as studies on histological distributions of drugs and/or substrates. For example, radioactive isotopes such as tritium ($^{3}H$) and carbon 14 ($^{14}C$) can be used for this purpose in view of ease of labeling and convenience in detection. Replacement by a heavier isotope, for example, replacement of hydrogen by heavy hydrogen ($^{2}H$) may be therapeutically advantageous (e.g. increase the half-life in vivo, decrease the necessary dose or decrease drug interaction) because metabolic stability is improved. Replacement by positron-emitting isotopes (e.g. $^{11}C$, $^{18}F$, $^{15}O$ and $^{13}N$) can be used in positron emission topography (PET) tests for examining the substrate receptor occupancy. In general, the isotopically labeled compound of the present invention can be produced by a conventional method known to a person skilled in the art, or the same production method as in Examples or Production Examples using an isotopically labeled appropriate reagent instead of a non-labeled reagent.

In the present specification, if the term "near" is included in the description of the diffraction angle (2θ (°)) in the powder X-ray diffraction pattern and the onset temperature (° C.) of the endothermic peak in the DSC analysis, it means that the error range is included, which is approximately the onset value of the diffraction angle and the endothermic peak, respectively. The error range of the diffraction angle (2θ (°)) in powder X-ray diffraction is ±0.2° in one embodiment and ±0.1° in yet another embodiment. The error range of the endothermic peak onset temperature (° C.) in the DSC analysis is ±2° C. in one embodiment and ±1° C. in yet another embodiment.

Due to the nature of the data, crystal lattice spacing or overall pattern of the powder X-ray diffraction pattern is important in determining crystal identity. The diffraction angles and diffraction intensities may change to some extent depending on direction of crystal growth, particle size and measurement conditions.

(Production Method)

A compound of formula (I) or a salt thereof can be produced using any of a variety of known synthesis methods with the utilization of characteristics based on the basic structure or the types of substituents. Here, depending on the type of a functional group, replacement of the functional group by an appropriate protecting group (a group easily convertible into the functional group) in the step of forming an intermediate from a starting material may be effective in terms of a production technique. Examples of the protecting group include protecting groups as described in P. G. M. Wuts and T. W. Greene, "Greene's Protective Groups in Organic Synthesis (4th edition, 2006)", and a protecting group may be appropriately selected according to relevant reaction conditions. In this method, a desired compound can be prepared by introducing the protecting group to carry out reaction, and then removing the protecting group as necessary.

The prodrug of a compound (I) can be produced by introducing a specific group in the step of forming an intermediate from a starting material as with the above-described protecting group, or further carrying out reaction using the obtained compound of formula (I). The reaction can be carried out by using a usual method known to a person skilled in the art, such as esterification, amidation or dehydration.

Hereinafter, typical methods for producing a compound of formula (I) will be described. The production methods can be carried out with reference to the references cited in the description. The production method of the present invention is not limited to the examples shown below.

The following abbreviations may be used herein.

DMF: N,N-dimethylformamide, DMSO: dimethylsulfoxide, DIPEA: N,N-diisopropylethylamine, NMP: 1-methylpyrrolidine-2-one, Me: methyl, $PdCl_2(PPh_3)_2$; bis(triphenylphosphine)palladium (II) dichloride, $PdCl_2(dppf)/CH_2Cl_2$: [1,1'-bis(diphenylphosphino)ferrocene]palladium (II) dichloride/dichloromethane adduct, $Pd_2(dba)_3$: (1E,4E)-1,5-diphenylpenta-1,4-dien-3-one/palladium (3:2), $Pd(PPh_3)_4$: tetrakis (triphenylphosphine)palladium, RuPhos Pd G3: (2-dicyclohexylphosphino-2',6'-diisopropoxy-1,1'-biphenyl)[2-(2'-amino-1,1'-biphenyl)]palladium (II) methanesulfonate, THF: tetrahydrofuran, TFA: trifluoroacetic acid, TMS: trimethylsilyl.

(First Production Method)

[Formula 8]

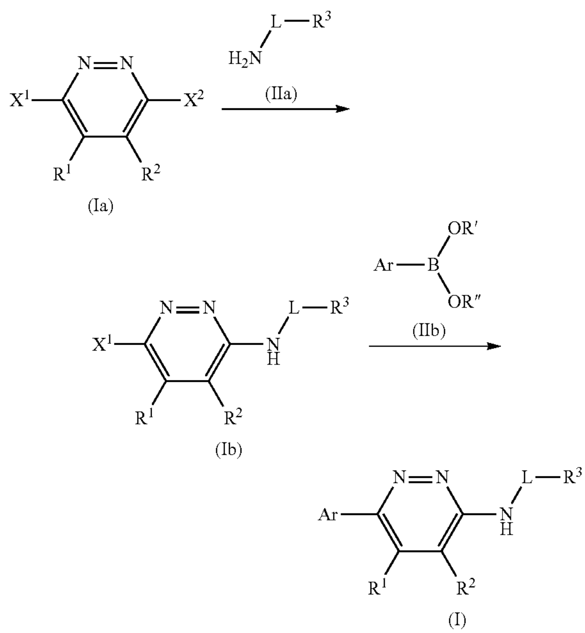
(Ia)
(IIa)
(Ib)
(IIb)
(I)

($X^1$ and $X^2$ are the same or different, and each are Cl, Br or I. Both R' and R" are H, or R' and R" together form 4,4,5,5-tetramethyl-1,3,2-dioxaborane. The same applies hereinafter.)

(First Step)

This step is a step of preparing a compound of formula (Ib) by reaction of a compound of formula (Ia) with a compound of formula (IIa). In this reaction, the compound of formula (Ia) and the compound of formula (IIa) are used in equal amount, or one of the compounds is used in excessive amount. A mixture of these compounds is stirred preferably at room temperature to 190° C. typically for 0.1 hours to 5 days under cooling or heating to reflux in a solvent inactive to the reaction or without the presence of a solvent. Examples of the solvent used here include, but are not limited to, ethers such as diethyl ether, THF, 1,4-dioxane, 1,2-dimethoxyethane, alcohols such as methanol, ethanol, 1-propanol, 2-propanol and 1-butanol, water, pyridine, acetonitrile, NMP, DMF, DMSO and mixtures thereof. It may be advantageous to carry out the reaction in the presence of an organic base such as triethylamine or N,N-diisopropylethylamine, or an inorganic base such as potassium carbonate, sodium carbonate or cesium carbonate for the reaction to smoothly proceed. This reaction may be carried out under microwave irradiation.

(Second Step)

This step is a step of preparing a compound of formula (I) by reaction of a compound of formula (Ib) with a compound of formula (IIb). In this reaction, the compound of formula (Ib) and the compound of formula (IIb) are used in equal amount, or one of the compounds is used in excessive amount. A mixture of these compounds is stirred preferably at room temperature to 150° C. typically for 0.1 hours to 5 days under cooling or heating to reflux in the presence of a catalyst and a base in a solvent inactive to the reaction. Examples of the catalyst used here include, but are not limited to, $Pd(PPh_3)_4$, $PdCl_2(PPh_3)_2$, $PdCl_2(dppf)/CH_2Cl_2$, $Pd_2(dba)_3$ and RuPhos Pd G3. Examples of the base include, but are not limited to, tripotassium phosphate, sodium carbonate, potassium carbonate, cesium carbonate, sodium hydroxide and sodium-t-butoxide. Examples of the solvent include, but are not limited to, ethers such as diethyl ether, THF, 1,4-dioxane and 1,2-dimethoxyethane, aromatic hydrocarbons such as benzene, toluene and xylene, and water, pyridine, acetonitrile, NMP, DMF, DMSO and mixtures thereof. This reaction may be carried out under microwave irradiation.

(Second Production Method)

[Formula 9]

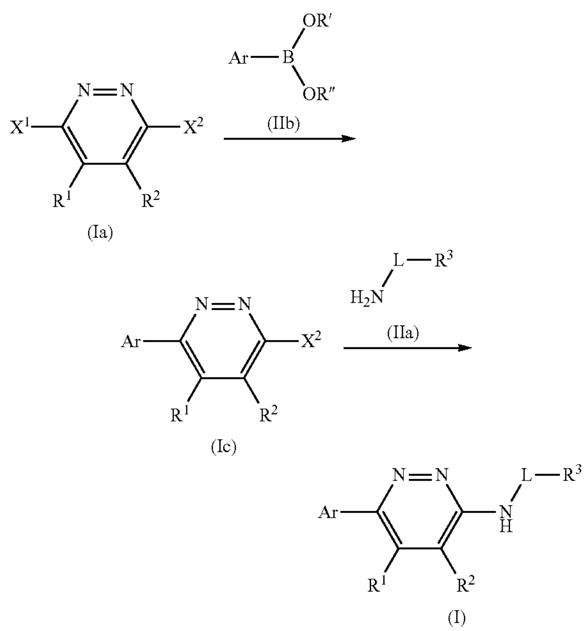

(First Step)

This step is a step of preparing a compound of formula (Ic) by reaction of a compound of formula (Ia) with a compound of formula (IIb). In this reaction, the compound of formula (Ia) and the compound of formula (IIb) are used in equal amount, or one of the compounds is used in excessive amount. A mixture of these compounds is stirred preferably at room temperature to 150° C. typically for 0.1 hours to 5 days under cooling or heating to reflux in the presence of a catalyst and a base in a solvent inactive to the reaction. Examples of the catalyst used here include, but are not limited to, $Pd(PPh_3)_4$, $PdCl_2(PPh_3)_2$, $PdCl_2(dppf)/CH_2Cl_2$, $Pd_2(dba)_3$ and RuPhos Pd G3. Examples of the base include, but are not limited to, tripotassium phosphate, sodium carbonate, potassium carbonate, cesium carbonate, sodium hydroxide and sodium-t-butoxide. Examples of the solvent include, but are not limited to, ethers such as diethyl ether, THF, 1,4-dioxane and 1,2-dimethoxyethane, aromatic hydrocarbons such as benzene, toluene and xylene, and water, pyridine, acetonitrile, NMP, DMF, DMSO and mixtures thereof. This reaction may be carried out under microwave irradiation.

(Second Step)

This step is a step of preparing a compound of formula (I) by reaction of a compound of formula (Ic) with a compound of formula (IIa). In this reaction, the compound of formula (Ic) and the compound of formula (IIa) are used in equal amount, or one of the compounds is used in excessive amount. A mixture of these compounds is stirred preferably at room temperature to 190° C. typically for 0.1 hours to 5 days under cooling or heating to reflux in a solvent inactive to the reaction or without the presence of a solvent. Examples of the solvent used here include, but are not limited to, ethers such as diethyl ether, THF, 1,4-dioxane, 1,2-dimethoxyethane, alcohols such as methanol, ethanol, 1-propanol, 2-propanol and 1-butanol, water, pyridine, acetonitrile, NMP, DMF, DMSO and mixtures thereof. It may be advantageous to carry out the reaction in the presence of an organic base such as triethylamine or N,N-diisopropylethylamine, or an inorganic base such as potassium carbonate, sodium carbonate or cesium carbonate for the reaction to smoothly proceed. This reaction may be carried out under microwave irradiation.

(Other Production Methods)

By using as a starting material a compound of formula (I) prepared by any of the above-described production methods and carrying out chemical modification reaction such as esterification or amidation, which is typically employed by a person skilled in the art, another compound of formula (I) can be prepared.

A compound of formula (I) is isolated in the form of a free compound, or a salt, a hydrate, a solvate or a crystal-polymorphic substance thereof, and purified. A salt of a compound of formula (I) can be produced by carrying out conventional salting reaction. The isolation and purification is performed by applying usual chemical operations such as extraction, fractionated crystallization and various kinds of fractionating chromatography. Various isomers can be produced by selecting appropriate compounds as a starting material, or isolated with the utilization of a difference in physicochemical properties between isomers. For example, an optical isomer can be obtained by a general method for optical resolution of a racemate (e.g. fractionated crystallization for forming a diastereoisomer salt with an optically active base or acid, or chromatography using a chiral column or the like), or produced from an appropriate optically active compound as a starting material.

The pharmacological activity of a compound of formula (I) can be examined by the following test or a well-known modified test.

Test Example 1: Test on IL-1β Production of THP-1

50 ng/mL of PMA (phorbol myristate acetate, SIGMA, P1585) was added to THP-1 cells, and the cells were cultured at 37° C. for 2 days. The culture solution was replaced by serum-free RPMI-1640 culture medium, a compound with a known concentration was added, and the cells were cultured at 37° C. for 15 minutes. LPS (Lipopolysaccharide, SIMGA, L2880) and ATP (Adenosine triphosphate, SIGMA, A2383) were added to final concentrations of 50 ng/mL and 5 mM, respectively, and the cells were cultured at 37° C. for 2 hours. The supernatant was collected, and the concentration of IL-1β was measured by an ELISA method (DuoSet ELISA human IL-1β, R&D Systems, DY201). The inhibition ratio at each concentration was determined, where the amount of IL-1β produced with no addition of the test compound or the stimulating substance (LPS and ATP) was defined as 100% inhibition and the amount of IL-1β produced with no addition of the test compound and with addition of the stimulating substance was defined as 0% inhibition. The $IC_{50}$ value was calculated by sigmoid Exam model non-linear regression analysis.

Table 1 shows the results. It was confirmed that the example compound inhibits IL-1β production.

TABLE 1

| Ex | $IC_{50}$ (nM) |
|---|---|
| 1 | 980 |
| 2 | 1800 |
| 3 | 120 |
| 4 | 210 |
| 5 | 200 |
| 6 | 90 |
| 7 | 17 |
| 8 | 160 |
| 9 | 14 |
| 10 | 200 |
| 11 | 150 |
| 12 | 150 |
| 13 | 120 |
| 14 | 330 |
| 15 | 97 |
| 16 | 200 |
| 17 | 110 |
| 18 | 260 |
| 19 | 610 |
| 20 | 1500 |
| 21 | 160 |
| 22 | 530 |
| 23 | 120 |
| 24 | 560 |
| 25 | 500 |
| 26 | 54 |
| 27 | 190 |
| 28 | 200 |
| 29 | 460 |
| 30 | 510 |
| 31 | 270 |
| 32 | 11 |
| 33 | 170 |
| 34 | 21 |
| 35 | 590 |
| 36 | 620 |
| 37 | 33 |
| 38 | 9.5 |
| 39 | 750 |
| 40 | 240 |
| 41 | 200 |
| 42 | 1500 |
| 43 | 860 |
| 44 | 570 |
| 45 | 530 |
| 46 | 120 |
| 47 | 400 |
| 48 | 510 |
| 49 | 680 |
| 50 | 1100 |
| 51 | 990 |
| 52 | 470 |
| 53 | 2700 |
| 54 | 3500 |
| 55 | 5100 |

TABLE 1-continued

| Ex | $IC_{50}$ (nM) |
|---|---|
| 56 | 2500 |
| 57 | 1600 |
| 58 | 950 |
| 59 | 750 |
| 60 | 1700 |
| 61 | 1500 |
| 62 | 2100 |
| 63 | 8.4 |
| 64 | 33 |
| 65 | 49 |
| 66 | 47 |
| 67 | 170 |
| 68 | 310 |
| 69 | 250 |
| 70 | 36 |
| 71 | 38 |
| 72 | 17 |
| 73 | 43 |
| 74 | 35 |
| 75 | 18 |
| 76 | 26 |
| 77 | 89 |
| 78 | 43 |
| 79 | 340 |
| 80 | 7.0 |

Test Example 2: Test on IL-1β Production in Rat Central Nerve

To a 10 to 14-week-old male Wistar rat, 12.5 μg/5 μL of LPS (SIGMA L2880) was intracisternally administered under anesthesia with isoflurane. After 2 hours, the test compound was orally administered. After 1 hour, 50 μg/5 μL of BzATP (2'(3')—O-(4-Benzoylbenzoyl)adenosine 5'-triphosphate triethylammonium salt, SIGMA, B6396) was intracisternally administered, and after 30 minutes, a cerebral spinal fluid was collected. The amount of IL-1β p17 in the cerebral spinal fluid was determined by a Western blotting method using an anti-IL-1β antibody (Millipore, AB1832P), and the inhibition ratio to the solvent administration group was calculated.

Table 2 shows the IL-1β p17 inhibition ratios to the solvent administration group, in Examples 4, 9 and 63, which are for compounds of formula (I). In the table, Dose represents a dose of each test compound, Ex4, Ex9 and Ex63 represent Example 4, Example 9 and Example 63, respectively, and NT represents a case where measurement was not performed. It is confirmed that these compounds exhibit an inhibitory action on IL-1β production in vivo.

TABLE 2

| Dose | Ex4 | Ex9 | Ex63 |
|---|---|---|---|
| 0.3 mg/kg | NT | 37% | 60% |
| 1 mg/kg | NT | 70% | 69% |
| 3 mg/kg | 68% | 89% | 66% |
| 10 mg/kg | 93% | NT | NT |
| 30 mg/kg | 100% | NT | NT |

Test Example 3: Mouse Cuprizone-Induced Neuroinflammation Model

Male C57BL/6J mice were fed a diet containing 0.2% Cuprizone (ENVIGO, TD.140801) for 40 days. The test compound was suspended in a 0.5% methylcellulose solution and orally administered at doses of 1 and 3 mg/kg once daily from the beginning day of administration of Cuprizone. To a negative control group, 0.5% methylcellulose solution was administered. Movement function was evaluated by the hanging wire test (van Putten M. 'The use of hanging wire tests to monitor muscle strength and condition over time.', [Online], May 2019, TREAT-NMD, Experimental protocols for DMD animal models, DMD_M.2.1.004, retrieved from the internet: <URL: http://www.treat-nmd.eu/research/preclinical/dmd-sops/>). The time until the mouse grasping a horizontally-stretched wire falls was measured three times, and the average value was calculated. The results of evaluating the compounds of Example 63 in this test are shown in FIG. 1. The compounds of Example 63 significantly prolonged the time to fall in the 1 and 3 mg/kg administration groups compared to the negative control group. From this, it was confirmed that the compound of Example 63 showed an improving effect on movement disorders.

Test Example 4: Mouse α-Synuclein Fiber-Induced Neuroinflammation Model

Figure 2:
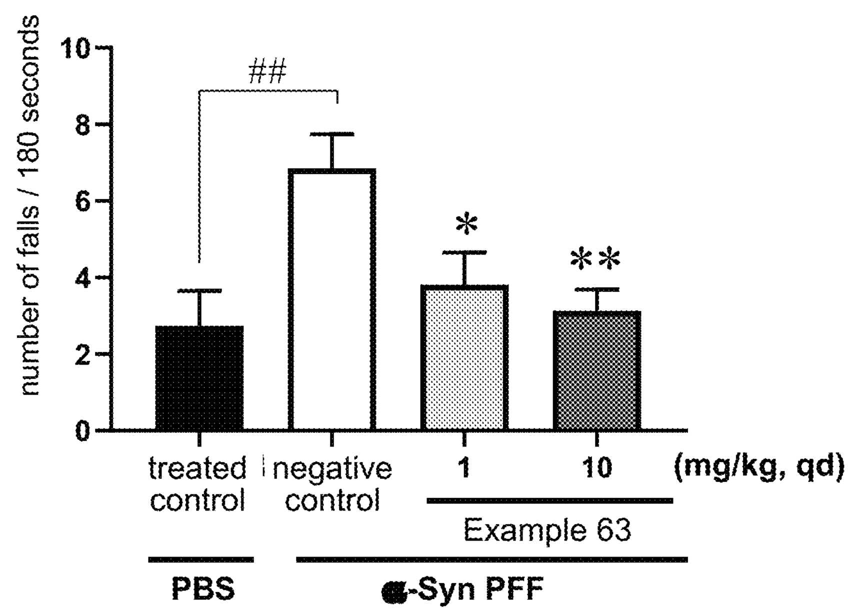
FIG. 2 shows results of the hanging wire test which evaluates an improving effect of the compound of the Example 63 to a movement disorder in α-synuclein fiber-induced neuroinflammation model.

To male C57BL/6J mice, 8 μg of mouse α-synuclein fibrotic protein (StressMarq Biosciences Inc., SPR-324) was administered to the left striatum. After 13-14 weeks, the test compound suspended in a 0.5% methylcellulose solution was orally administered once daily at a dose of 1 or 10 mg/kg. To a negative control group, 0.5% methylcellulose solution was administered. Movement function was evaluated by a hanging wire test 4 weeks after the start of administration. In this test, the mouse was hung at a horizontally stretched wire, and when it fell, it was hung again for 3 minutes, and the number of falls was recorded. The results of evaluating the compound of Example 63 in this test are shown in FIG. 2. The compound of Example 63 significantly reduced the number of falls in the 1 and 10 mg/kg administration groups as compared with the negative control group. From this, it was confirmed that the compound of Example 63 showed an improving effect on movement disorders.

Test Example 5: Mouse Ex Vivo IL-1β Production Test

Figure 3:
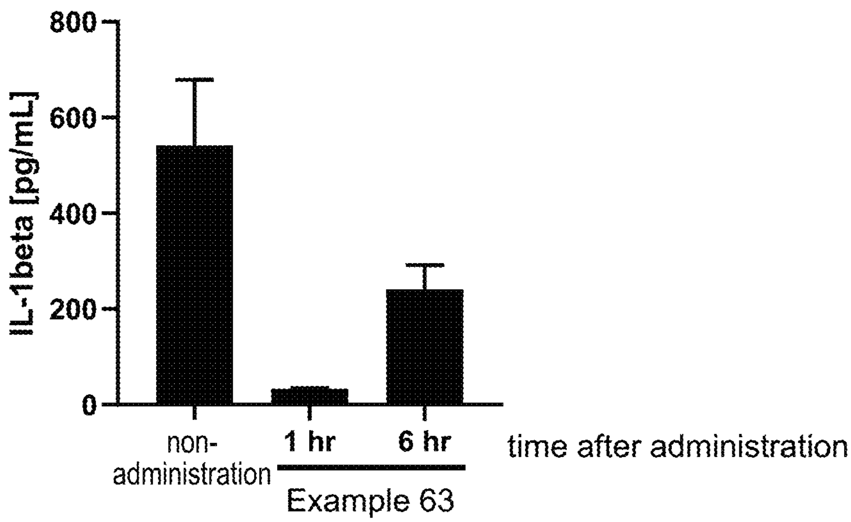
FIG. 3 shows results of the mouse ex vivo test which determines an amount of IL-1β produced when the compound of the Example 63 was administered.

Male C57BL/6J mice were orally administered with the compound suspended in 0.5% methylcellulose at a dose of 3 mg/kg, and blood was collected 1 hour and 6 hours later. LPS was added to the blood to a final concentration of 50 ng/mL, which was cultured at 37° C. for 3 hours. Then, ATP was added to a final concentration of 5 mM, which was cultured at 37° C. for 30 minutes. After removing blood cells by centrifugation, the concentration of IL-1β was measured by the ELISA method (DuoSet ELISA mouse IL-1β, R & D Systems, DY401). The results of evaluating the compound of the Example 63 in this test are shown in FIG. 3. The compound of the Example 63 decreased the amount of IL-1β produced in the blood collected 1 hour and 6 hours after the administration of the compound.

Test Example 6: In Vitro Phototoxicity Test

The evaluation of in vitro phototoxicity tests is based on ICH S10: Guidelines for Evaluation of Phototoxicity of Drugs (Notification No. 0521-1) and OECD guideline for testing of chemicals 432: In vitro 3T3 NRU phototoxicity test, 2004, which is described in the OECD report. In this test, it was confirmed that the compound of Example 63 had no phototoxic effect.

Test Example 7: Safety Pharmacology Test

As a safety pharmacological test, the human Ether-a-go-go Related Gene (hereinafter referred to as hERG) channel inhibitory effect was evaluated. The hERG channel inhibitory effect was evaluated using a modified method described in Combinatorial Chemistry & High Throughput Screening, 12, 1, 78-95 (2009). In this study, the compound of Example 63 showed an $IC_{50}$ of 34.5 μM.

From the above results, it is expected that a compound of formula (I) or a salt thereof can be used for prevention and/or treatment of an inflammatory disease, a neurodegenerative disease or the like.

It is known that the expression of NLRP3 and IL-1β is enhanced in the central nerve system in a model of multiple sclerosis induced by administration of cuprizone (The Journal of Neuroscience, vol. 30, no. 47, pages 15811-15820). In addition, it is known that α-synuclein fibers activate NLRP3 to promote IL-1β production from microglia, and that, in a model of α-synucleinopathy induced by α-synuclein fibers, improvements were confirmed administration of an NLRP3 inhibitor (Science Translational Medicine, vol. 10, article number eaah4066, 2018).

The compound of formula (I) or a salt thereof shown in Table 1 was shown to suppress the production of IL-1β (Test Example 1), and the compounds of Examples 4, 9, and 63 were shown to have an IL-1β production inhibitory effect in the central nervous system (Test Example 2). Further, it was confirmed that the compound of Example 63 showed an improving effect on movement disorders in the mouse cuprizone-induced neuroinflammation model of Test Example 3 and the mouse α-synuclein fiber-induced neuroinflammation model of Test Example 4. From the above results, it is strongly expected that the compound of formula (I) or a salt thereof is useful for prevention and/or treatment of neurodegenerative diseases, particularly multiple sclerosis, and α-synucleinopathy including Parkinson's disease, multiple system atrophy and Lewy body dementias.

Also, from the results of Test Example 5, it was shown that the compound of Example 63 suppressed IL-1β production even in the blood 6 hours after oral administration. Further, from the results of Test Examples 6 and 7, it was shown that the compound of Example 63 has no phototoxic effect and shows a weak hERG channel inhibitory effect. From the above results, it is strongly expected that the compound of Example 63 will be a drug having excellent durability and high safety as an oral preparation.

A pharmaceutical composition comprising one or more compounds of formula (I) or salts thereof as an active ingredient can be prepared by a commonly used method with the use of excipients which are commonly used in the field, specifically, pharmaceutical excipients and pharmaceutical carriers.

The administration may be either oral administration of tablets, pills, capsules, granules, powders, solutions and the like or parenteral administration of injection preparations for intraarticular administration, intravenous administration, intramuscular administration and the like, suppositories, eye-drops, ophthalmic ointments, transdermal solutions, ointments, transdermal patches, transmucosal solutions, transmucosal patches, inhalants and the like.

As a solid composition for oral administration, a tablet, a powder, a granule or the like is used. In such a solid composition, one or more active ingredients are mixed with at least one inactive excipient. The composition may contain inactive additives, for example a lubricant, a disintegrant, a stabilizer and a solubilizer, in accordance with a conventional method. The tablet, powder, granule or pill may be covered with a film of wax, a sugarcoating or a stomach-soluble or enteric substance.

The liquid composition for oral administration contains a pharmaceutically acceptable opacifier, solution, suspension, syrup, elixir or the like, and an inactive diluent which is generally used, for example purified water or ethanol. The liquid composition may contain, in addition to the inactive diluent, adjuvants such as a solubilizing agent, a wetting agent and a suspending agent, a sweetening agent, a flavoring agent, a fragrance and a preservative.

The injection preparation for parenteral administration contains a sterile aqueous or nonaqueous solution, suspension or opacifier. Examples of the aqueous solvent include distilled water for injection and physiological saline. Examples of the nonaqueous solvent include alcohols such as ethanol. Such a composition may further contain a tonicity agent, a preservative, a wetting agent, an emulsifier, a dispersant, a stabilizer or a solubilizer. Such an agent is sterilized by, for example, filtration through a bacteria retaining filter, addition of a bactericide or irradiation. Such an agent may be dissolved or suspended in sterile water or a sterile solvent for injection before a sterile solid composition is produced and used.

External preparations include ointments, plasters, creams, jellies, cataplasms, sprays, lotions, eye-drops and ophthalmic ointments. The external preparation contains an ointment base, a lotion base, an aqueous or nonaqueous solution, a suspension, an emulsion or the like.

The transmucosal such as an inhalant or transnasal preparation, which is solid, liquid or semisolid, can be produced in accordance with a known method. For example, a known excipient, and a pH adjuster, a preservative, a surfactant, a lubricant, a stabilizer, a thickener and the like may be appropriately added. For administration, an appropriate device for inhalation or insufflation may be used. For example, using a known device such as an inhalation device for metered administration or a nebulizer, the compound can be administered alone, as powder of a formulated mixture, or as a solution or a suspension containing a pharmaceutically acceptable carrier in combination with the compound. A dry powder inhaler or the like may be one for single administration or multiple administration, and dry powder or a powder-containing capsule may be used for the inhaler. Alternatively, the inhaler may be in the form of a pressurized aerosol spray or the like using an appropriate ejection agent, for example a suitable gas such as chlorofluoroalkane or carbon dioxide.

Normally, in the case of oral administration, the suitable daily dose body weight is about 0.001 to 100 mg/kg, preferably 0.1 to 30 mg/kg, more preferably 0.1 to 10 mg/kg, and is given once or in two to four parts. In the case of intravenous administration, the suitable daily dose per body weight is about 0.0001 to 10 mg/kg, and is given once or in two or more parts daily. For the transmucosal preparation, a dose of about 0.001 to 100 mg/kg body weight is given once or in two or more parts daily. The dose is appropriately determined according to an individual case with consideration given to properties, an age, a sex and the like.

The pharmaceutical composition of the present invention comprises 0.01 to 100 wt %, or 0.01 to 50 wt % in an embodiment, of one or more compounds of formula (I) or salts thereof as active ingredients, depending on the administration route, the dosage form, the administration site and the types of excipients and additives.

The compound of formula (I) may be used in combination with any of various therapeutic agents or prophylactic agents for diseases on which the compound of formula (I) may be effective. The combined administration may be performed simultaneously, separately and successively, or at a desired time interval. Simultaneous administration preparations may be combination preparations or separately formulated preparations.

EXAMPLES

Hereinafter, the method for producing a compound of formula (I) will be described in more detail on the basis of Examples. The present invention is not limited to the compounds described in Examples below. Also, the method for producing a compound as a starting material will be described in Production Examples. The method for producing a compound of formula (I) is not limited to the production methods of specific Examples shown below, and the compound of formula (I) can be produced by a combination of these production methods, or methods obvious to a person skilled in the art.

The onset temperature of the DSC curve obtained by measuring under the following conditions is shown in the table below as the melting point. DSC was measured using an aluminum sample pan and DSC Q2000 (manufactured by TA Instruments) under the conditions of measurement temperature range: room temperature to 300° C., heating rate: 10° C./min, nitrogen flow rate: 50 mL/min. The measurement was performed without the lid on the sample pan.

Powder X-ray diffraction was measured using Empyrean (manufactured by PANalytical) under the conditions of tube: Cu, tube current: 40 mA, tube voltage: 45 kV, step width: 0.013°, wavelength: 1.5418 Å, measurement diffraction angle range (2θ): 2.5-40°. Due to the nature of the data, the crystal lattice spacing and overall pattern of the powder X-ray diffraction pattern are important in determining crystal identity. The error range of the diffraction angle (2θ (°)) in powder X-ray diffraction is usually ±0.2°, but the diffraction angle and diffraction intensity should not be strictly understood, which may vary to some extent depending on direction of crystal growth, particle size, and measurement conditions.

The following abbreviations may be used in Examples, Production Examples and the tables below.

PEx: Production Example No., Ex: Example No., PSyn: Production Example No. where compounds are produced by the same method, Syn: Example No. where compounds are produced by the same method, Str: chemical structural formula, DAT: physicochemical data, ESI+: m/z value in mass spectrometry (ionization method ESI, [M+H]+ unless otherwise specified), APCI/ESI+: APCI/ESI-MS (atmospheric chemical ionization method APCI, APCI/ESI means simultaneous measurement of APCI and ESI, [M+H]+ unless otherwise specified), API-ES+: API-ES MS (atmospheric ionization-electrospray method, [M+H]+ unless otherwise specified), J: coupling constant, s: singlet, d: doublet, t: triplet, q: quartet, dd: double doublet, ddd: double double doublet, tt: triple triplet, br: broad line (e.g. br s), m: multiplet, m.p.: melting point, 2θ: diffraction angle of peaks in powder X-ray diffraction.

Among compounds with a conformation in the chemical structural formula in the tables below, compounds indicated with "#" have a relative conformation as the written conformation, and other compounds have an absolute conformation as the written conformation.

Compounds whose names are preceded by “rac” are racemates.

The concentration (mol/1) is expressed in M for convenience. For example, the aqueous solution of 1 M sodium hydroxide solution means an aqueous solution of sodium hydroxide at 1 mol/1.

Production Example 1

A mixture of 2-(trimethylsilyl)ethanol (4.3 mL) and THF (100 mL) was cooled with ice, sodium hydride (60%, liquid paraffin dispersion, 1.2 g) was then added in an argon atmosphere, and the mixture was stirred at the same temperature for 10 minutes. To the obtained mixture was added dropwise a mixture of 3,4,6-trichloropyridazine (5.0 g) and THF (25 mL) under cooling with ice, and the mixture was stirred at room temperature for 30 minutes. Water and a saturated aqueous solution of sodium chloride were added to the reaction mixture, followed by extraction with ethyl acetate. The organic layer was washed with a saturated aqueous solution of sodium chloride, and then dried over anhydrous magnesium sulfate. The solution was concentrated under reduced pressure, and the obtained residue was then purified by silica gel column chromatography (hexane/ethyl acetate) to give 3,6-dichloro-4-[2-(trimethylsilyl)ethoxy]pyridazine (2.9 g) as a solid.

Production Example 2

A mixture of 3,4,6-trichloropyridazine (2.5 g), potassium carbonate (2.3 g), 18-crown-6 (0.32 g), benzene (15 mL) and 2-(benzyloxy)ethanol (2.3 g) was stirred overnight in an argon atmosphere at 70° C. The reaction mixture was allowed to cool to room temperature, ethyl acetate was then added, and the mixture was filtered. The filtrate was concentrated under reduced pressure, and the obtained residue was then purified by silica gel column chromatography (hexane/ethyl acetate) to give 4-[2-(benzyloxy)ethoxy]-3,6-dichloropyridazine (3.4 g) as an oily material.

Production Example 3

A mixture of 3,6-dichloro-4,5-dimethylpyridazine (340 mg), NMP (5 mL), (2R)-1-aminopropan-2-ol (0.23 mL) and potassium carbonate (400 mg) was stirred overnight at 100° C. The reaction mixture was allowed to cool to room temperature, and water was then added, followed by extraction with ethyl acetate. The organic layer was dried over anhydrous magnesium sulfate. The solution was concentrated under reduced pressure, and the obtained residue was then purified by silica gel column chromatography (chloroform/methanol) to give (2R)-1-[(6-chloro-4,5-dimethylpyridazin-3-yl)amino]propan-2-ol (39 mg) as a solid.

Production Example 4

A mixture of 3,6-dichloro-4-methylpyridazine (4.0 g), isopropylalcohol (30 mL), (2R)-1-aminopropan-2-ol (6 mL) and DIPEA (12 mL) was divided into three equal portions, and the mixtures were then stirred under microwave irradiation at 140° C. for 3 hours. The reaction mixtures were mixed, and concentrated under reduced pressure. Ethyl acetate and a saturated aqueous solution of sodium bicarbonate were added to the obtained residue, followed by extraction with ethyl acetate. The organic layer was washed with a saturated aqueous solution of sodium chloride, and dried over anhydrous magnesium sulfate. The solution was concentrated under reduced pressure, and the obtained residue was then purified by basic silica gel column chromatography (hexane/ethyl acetate) to give (2R)-1-[(6-chloro-5-methylpyridazin-3-yl)amino]propan-2-ol (2.4 g) and (2R)-1-[(6-chloro-4-methylpyridazin-3-yl)amino]propan-2-ol (1.0 g) as solids, respectively.

Production Example 24

$PdCl_2(PPh_3)_2$ (0.31 g) was added to a mixture of 3,6-dichloro-4-phenylpyridazine (1.0 g), [4-(trifluoromethyl)phenyl]boronic acid (0.84 g), sodium carbonate (1.4 g), 1,2-dimethoxyethane (21 mL) and water (4 mL) in a nitrogen atmosphere, and the mixture was stirred at 80° C. for 16 hours. Water was added to the reaction mixture, followed by extraction with ethyl acetate. The organic layer was dried over anhydrous sodium sulfate. The solution was concentrated under reduced pressure, and the obtained residue was then purified by silica gel column chromatography (hexane/ethyl acetate) to give 6-chloro-4-phenyl-3-[4-(trifluoromethyl)phenyl]pyridazine (0.15 g) and 3-chloro-4-phenyl-6-[4-(trifluoromethyl)phenyl]pyridazine (0.70 g) as solids, respectively.

Production Example 25

Acetic anhydride (0.57 mL) and N,N-dimethyl-4-aminopyridine (120 mg) were added to a mixture of (2R)-1-[(6-chloro-5-methylpyridazin-3-yl)amino]propan-2-ol (1.0 g), dichloromethane (10 mL) and triethylamine (2.1 mL) at room temperature, and the mixture was stirred overnight at the same temperature. Water was added to the reaction mixture, followed by extraction with ethyl acetate. The organic layer was dried over anhydrous magnesium sulfate. The solution was concentrated under reduced pressure, and the obtained residue was then purified by silica gel column chromatography (hexane/ethyl acetate). To the obtained purified product was added hexane and ethyl acetate, followed by trituration. The precipitated solid was collected by filtration to give (2R)-1-[(6-chloro-5-methylpyridazin-3-yl)amino]propan-2-yl acetate (1.1 g) as a solid.

Production Example 26

A mixture of (2R)-1-({6-chloro-4-[2-(trimethylsilyl)ethoxy]pyridazin-3-yl}amino)propan-2-ol (800 mg), [2,4-bis(trifluoromethyl)phenyl]boronic acid (1.2 g), potassium carbonate (730 mg), water (1.6 mL), 1,4-dioxane (16 mL) and RuPhos Pd G3 (220 mg) was stirred in an argon atmosphere at 100° C. for 3 hours. The reaction mixture was allowed to cool to room temperature, and water was then added, followed by extraction with ethyl acetate. The organic layer was washed with a saturated aqueous solution of sodium chloride, and then dried over anhydrous magnesium sulfate. The solution was concentrated under reduced pressure, and the obtained residue was then purified by silica gel column chromatography (hexane/ethyl acetate) to give (2R)-1-({6-[2,4-bis(trifluoromethyl)phenyl]4-[2-(trimethylsilyl)ethoxy]pyridazin-3-yl}amino)propan-2-ol (1.0 g) as a solid.

Production Example 30

TFA (5 mL) was added to a mixture of t-butyl [4-({6-[2,4-bis(trifluoromethyl)phenyl]pyridazin-3-yl}amino)butyl]

carbamate (700 mg) and dichloromethane (10 mL) in a nitrogen atmosphere at room temperature, and the mixture was stirred at the same temperature for 16 hours. The reaction mixture was concentrated under reduced pressure. To the obtained residue was added a saturated aqueous solution of sodium bicarbonate, followed by extraction with ethyl acetate. The organic layer was washed with a saturated aqueous solution of sodium chloride, and then concentrated under reduced pressure to give $N^1$-{6-[2,4-bis(trifluoromethyl)phenyl]pyridazin-3-yl}butane-1,4-diamine (780 mg).

Production Example 32

Acetic anhydride (0.24 mL) and N,N-dimethyl-4-aminopyridine (51 mg) were added to a mixture of (2R)-1-({6-[2,4-bis(trifluoromethyl)phenyl]-4-[2-(trimethylsilyl)ethoxy]pyridazin-3-yl}amino)propan-2-ol (1.0 g), dichloromethane (10 mL) and triethylamine (0.88 mL) at room temperature, and the mixture was stirred at the same temperature for 30 minutes. Water and a saturated aqueous solution of sodium chloride were added to the reaction mixture, followed by extraction with ethyl acetate. The organic layer was dried with anhydrous magnesium sulfate. The solution was concentrated under reduced pressure, and the obtained residue was purified by silica gel column chromatography (hexane/ethyl acetate) to give (2R)-1-({6-[2,4-bis(trifluoromethyl)phenyl]-4-[2-(trimethylsilyl)ethoxy]pyridazin-3-yl}amino)propan-2-yl acetate (1.0 g) as an oily material.

Production Example 33

Tetrabutylammonium fluoride (1 M THF solution, 5.9 mL) was added to a mixture of (2R)-1-({6-[2,4-bis(trifluoromethyl)phenyl]-4-[2-(trimethylsilyl)ethoxy]pyridazin yl}amino)propan-2-yl acetate (1.0 g) and THF (10 mL) at room temperature, and the mixture was stirred at the same temperature for 30 minutes. Water was added to the reaction mixture, followed by extraction with ethyl acetate. The organic layer was washed with a saturated aqueous solution of sodium chloride, and dried over anhydrous magnesium sulfate. The solution was concentrated under reduced pressure to give (2R)-1-({6-[2,4-bis(trifluoromethyl)phenyl]-4-hydroxypyridazin-3-yl}amino)propan-2-yl acetate (820 mg) as a solid.

Production Example 34

Sodium chloro(difluoro)acetate (220 mg) and cesium carbonate (460 mg) were added to a mixture of (2R)-1-({6-[2,4-bis(trifluoromethyl)phenyl]-4-hydroxypyridazin-3-yl}amino)propan-2-yl acetate (200 mg) and DMF (4 mL) at room temperature, and the mixture was stirred at 90° C. for 1 hour. The reaction mixture was allowed to cool to room temperature, and water was then added, followed by extraction with ethyl acetate. The organic layer was washed with a saturated aqueous solution of sodium chloride, and then dried over anhydrous magnesium sulfate. The solution was concentrated under reduced pressure, and the obtained residue was then purified by silica gel column chromatography (chloroform/methanol). The obtained purified product was purified by silica gel column chromatography (hexane/ethyl acetate) to give (2R)-1-({6-[2,4-bis(trifluoromethyl)phenyl]-4-(difluoromethoxy)pyridazin-3-yl}amino)propan-2-yl acetate (110 mg) as an oily material.

Production Example 35

As a side product from the reaction in Example 3, 6-[2,4-bis(trifluoromethyl)phenyl]-3-{[(2R)-2-hydroxypropyl]amino}pyridazine-4-carboxylic acid (150 mg) was obtained as a solid.

Production Example 39

A mixture of 3,6-dichloro-4,5-dimethylpyridazine (300 mg), 1,4-dioxane (3 mL), (1R,2R)-2-aminocyclohexan-1-ol hydrochloride (510 mg) and DIPEA (0.87 mL) was stirred under microwave irradiation at 190° C. for 6 hours. Water was added to the reaction mixture, followed by extraction with chloroform. The organic layer was dried over anhydrous magnesium sulfate. The solution was concentrated under reduced pressure, and the obtained residue was then purified by silica gel column chromatography (chloroform/methanol) to give (1R,2R)-2-[(6-chloro-4,5-dimethylpyridazin yl)amino]cyclohexan-1-ol (150 mg) as a solid.

Example 1

A mixture of 6-chloro-4-phenyl-3-[4-(trifluoromethyl)phenyl]pyridazine (100 mg) and 3-aminopropan-1-ol (6 mL) was stirred under microwave irradiation at 120° C. for 1 hour. Water was added to the reaction mixture, followed by extraction with ethyl acetate. The organic layer was dried over anhydrous sodium sulfate. The solution was concentrated under reduced pressure, and the obtained residue was purified by silica gel column chromatography (dichloromethane/methanol) to give 3-({5-phenyl-6-[4-(trifluoromethyl)phenyl]pyridazin-3-yl}amino)propan-1-ol (60 mg) as a solid.

Example 3

Ethyl 6-chloro-3-{[(2R)-2-hydroxypropyl]amino}pyridazine-4-carboxylate (390 mg), [2,4-bis(trifluoromethyl)phenyl]boronic acid (580 mg), potassium carbonate (420 mg), water (1 mL), 1,4-dioxane (9 mL) and RuPhos Pd G3 (63 mg) were mixed and stirred under microwave irradiation at 100° C. for 1 hour in an argon atmosphere. The reaction mixture was concentrated under reduced pressure, and the obtained residue was then purified by silica gel column chromatography (chloroform/methanol). To the obtained purified product were added hexane and ethyl acetate, followed by trituration. The precipitated solid was taken by filtration to give ethyl 6-[2,4-bis(trifluoromethyl)phenyl]-3-{[(2R)-2-hydroxypropyl]amino}pyridazine-4-carboxylate (220 mg) as a solid.

Example 4

A mixture of (2R)-1-[(6-chloro-4,5-dimethylpyridazin-3-yl)amino]propan-2-ol (35 mg), [2,4-bis(trifluoromethyl)phenyl]boronic acid (75 mg), potassium carbonate (45 mg), water (0.20 mL), 1,4-dioxane (2 mL) and RuPhos Pd G3 (10 mg) was stirred in an argon atmosphere at 100° C. for 2 hours. The reaction mixture was allowed to cool to room temperature, and water was then added, followed by extraction with ethyl acetate. The organic layer was dried over anhydrous magnesium sulfate. The solution was concentrated under reduced pressure, and the obtained residue was then purified by silica gel column chromatography (chloroform/methanol) to give (2R)-1-({6-[2,4-bis(trifluoromethyl)phenyl]-4,5-dimethylpyridazin-3-yl}amino)propan-2-ol (60 mg) as a solid.

Example 5

A mixture of (2R)-1-[(6-chloro-5-methylpyridazin-3-yl)amino]propan-2-ol (300 mg), [2,4-bis(trifluoromethyl)phenyl]boronic acid (570 mg), potassium carbonate (400 mg), water (0.6 mL), 1,4-dioxane (6 mL) and RuPhos Pd G3 (61 mg) was stirred in an argon atmosphere at 100° C. for 2 hours. The reaction mixture was allowed to cool to room temperature, and then concentrated under reduced pressure. The obtained residue was purified by silica gel column chromatography (basic silica gel, hexane/ethyl acetate). To the obtained purified product was added ethyl acetate, followed by trituration. The precipitated solid was taken by filtration to give (2R)-1-({6-[2,4-bis(trifluoromethyl)phenyl]-5-methylpyridazin-3-yl}amino)propan-2-ol (290 mg) as a solid.

Example 6

A mixture of (2R)-1-[(6-chloro-4-methylpyridazin-3-yl)amino]propan-2-ol (140 mg), [2,4-bis(trifluoromethyl)phenyl]boronic acid (270 mg), potassium carbonate (190 mg), water (0.3 mL), 1,4-dioxane (3 mL) and RuPhos Pd G3 (29 mg) was stirred in an argon atmosphere at 100° C. for 2 hours. The reaction mixture was allowed to cool to room temperature, and then concentrated under reduced pressure. The obtained residue was purified by basic silica gel column chromatography (hexane/ethyl acetate). To the obtained purified product were added hexane and ethyl acetate, followed by trituration. The precipitated solid was taken by filtration to give (2R)-1-({6-[2,4-bis(trifluoromethyl)phenyl]-4-methylpyridazin-3-yl}amino)propan-2-ol (94 mg) as a solid.

Example 7

A mixture of (2R)-1-[(6-chloro-5-methylpyridazin-3-yl)amino]propan-2-ol (100 mg), [2-hydroxy-4-(trifluoromethyl)phenyl]boronic acid (160 mg), potassium carbonate (140 mg), water (0.20 mL), 1,4-dioxane (2 mL) and RuPhos Pd G3 (21 mg) was stirred in an argon atmosphere at 100° C. for 5 hours. The reaction mixture was allowed to cool to room temperature, and then concentrated under reduced pressure. The obtained residue was purified by silica gel column chromatography (chloroform/methanol). To the obtained purified product were added hexane and ethyl acetate, followed by trituration. The precipitated solid was collected by filtration to give 2-(6-{[(2R)-2-hydroxypropyl]amino}-4-methylpyridazin-3-yl)-5-(trifluoromethyl)phenol (90 mg) as a solid.

Example 8

A mixture of (2R)-1-[(6-chloro-4-methylpyridazin-3-yl)amino]propan-2-ol (100 mg), [2-hydroxy-4-(trifluoromethyl)phenyl]boronic acid (150 mg), potassium carbonate (140 mg), water (0.20 mL), 1,4-dioxane (2 mL) and RuPhos Pd G3 (21 mg) was stirred in an argon atmosphere at 100° C. for 5 hours. The reaction mixture was allowed to cool to room temperature, and then concentrated under reduced pressure. The obtained residue was purified by silica gel column chromatography (chloroform/methanol). To the obtained purified product were added hexane and ethyl acetate, followed by trituration. The precipitated solid was collected by filtration to give 2-(6-{[(2R)-2-hydroxypropyl]amino}-5-methylpyridazin-3-yl)-5-(trifluoromethyl)phenol (80 mg) as a solid.

Example 9

A mixture of (2R)-1-[(6-chloro-4,5-dimethylpyridazin-3-yl)amino]propan-2-ol (100 mg), [2-hydroxy-4-(trifluoromethyl)phenyl]boronic acid (140 mg), potassium carbonate (130 mg), water (0.20 mL), 1,4-dioxane (2 mL) and RuPhos Pd G3 (20 mg) was stirred in an argon atmosphere at 100° C. for 5 hours. The reaction mixture was allowed to cool to room temperature, and then concentrated under reduced pressure. The obtained residue was purified by silica gel column chromatography (chloroform/methanol). To the obtained purified product were added hexane and ethyl acetate, followed by trituration. The precipitated solid was collected by filtration to give 2-(6-{[(2R)-2-hydroxypropyl]amino}-4,5-dimethylpyridazin-3-yl)-5-(trifluoromethyl)phenol (110 mg) as a solid.

Example 40

A mixture of 6-[2,4-bis(trifluoromethyl)phenyl]-3-{[(2R)hydroxypropyl]amino}pyridazine-4-carboxylic acid (50 mg), DMF (1 mL), morpholine (0.022 mL), {{[1-cyano-2-ethoxy-2-oxoethylidene]amino}oxy}-4-morpholinomethylene]dimethylammoniumhexafluorophosphate (70 mg) and DIPEA (0.063 mL) was stirred at room temperature for 3 days. Water and a saturated aqueous solution of sodium chloride were added to the reaction mixture, followed by extraction with ethyl acetate. The organic layer was dried with anhydrous magnesium sulfate. The solution was concentrated under reduced pressure, and the obtained residue was then purified by silica gel column chromatography (chloroform/methanol) to give (6-[2,4-bis(trifluoromethyl)phenyl]-3-{[(2R)-2-hydroxypropyl]amino}pyridazin-4-yl)(morpholin-4-yl)methanone (20 mg) as a solid.

Example 42

DIPEA (0.18 mL) and trimethylaluminum (0.26 mL) were added to a mixture of methyl 6-[2,4-bis(trifluoromethyl)phenyl]-3-{[(2R)-2-hydroxypropyl]amino}pyridazine-4-carboxylate (150 mg), 1-methylpiperazine (53 mg) and toluene (15 mL) in a nitrogen atmosphere at room temperature, and the mixture was stirred at 80° C. for 12 hours. Water was added to the reaction mixture, followed by extraction with ethyl acetate. The organic layer was concentrated under reduced pressure, and the obtained residue was then purified by silica gel column chromatography (dichloromethane/methanol) to give (6-[2,4-bis(trifluoromethyl)phenyl]-3-{[(2R)-2-hydroxypropyl]amino}pyridazine-4-yl)(4-methylpiperazin-1-yl)methanone (40 mg) as a solid.

Example 45

Acetyl chloride (24 mg) and triethylamine (0.22 mL) were added to a mixture of (2R)—$N^1$-{6-[2,4-bis(trifluoromethyl)phenyl]pyridazin-3-yl}propane-1,2-diamine (100 mg) and dichloromethane (5 mL) in a nitrogen atmosphere at room temperature, and the mixture was stirred at the same temperature for 2 hours. Water was added to the reaction mixture, followed by extraction with ethyl acetate. The organic layer was concentrated under reduced pressure, and the obtained residue was then purified by silica gel column chromatography (dichloromethane/methanol) to give N-[(2R)-1-({6-[2,4-bis(trifluoromethyl)phenyl]pyridazin-3-yl}amino)propan-2-yl]acetoamide (42 mg) as a solid.

Example 46

Difluoroacetic acid (120 mg) and O-(7-azabenzotriazol-1-yl)-N,N,N',N'-tetramethyluroniumhexafluorophosphate (600 mg) and DIPEA (0.55 mL) were added to a mixture of $N^1$-{6-[2,4-bis(trifluoromethyl)phenyl]pyridazin-3-yl}butane-1,4-diamine (400 mg) and DMF (5 mL) in a nitrogen atmosphere at room temperature, and the mixture was stirred at the same temperature for 16 hours. Water was added to the reaction mixture, followed by extraction with ethyl acetate. The organic layer was concentrated under reduced pressure, and the obtained residue was then purified by silica gel column chromatography (dichloromethane/methanol). The obtained purified product was purified by reversed-phase silica gel column chromatography (0.02% aqueous TFA solution/acetonitrile) to give N-[4({6-[2,4-bis(trifluoromethyl)phenyl]pyridazin-3-yl}amino)butyl]-2,2-difluoroacetoamide (41 mg) as a solid.

Example 49

An aqueous solution of 1 M sodium hydroxide (0.49 mL) was added to a mixture of (2R)-1-({6-[2,4-bis(trifluoromethyl)phenyl]-4-(difluoromethoxy)pyridazin-3-yl}amino)propan-2-yl acetate (100 mg) and methanol (2 mL) at room temperature, and the mixture was stirred at the same temperature for 1.5 hours. 1 M hydrochloric acid (0.49 mL), water and a saturated aqueous solution of sodium hydroxide were added to the reaction mixture, followed by extraction with chloroform. The organic layer was dried over anhydrous magnesium sulfate. The solution was concentrated under reduced pressure, and the obtained residue was then purified by silica gel column chromatography (chloroform/methanol). To the obtained purified product were added ethyl acetate and a 4 M hydrogen chloride ethyl acetate solution (0.2 mL), and the mixture was concentrated under reduced pressure. Ethyl acetate was added to the obtained residue, and the precipitated solid was collected by filtration to give (2R)-1-({6-[2,4-bis(trifluoromethyl)phenyl]-4-(difluoromethoxy)pyridazin-3-yl}amino)propan-2-ol hydrochloride (54 mg) as a solid.

Example 63

(1R,2R)-2-[(6-chloro-4,5-dimethylpyridazin-3-yl)amino]cyclohexan-1-ol (150 mg), [2-hydroxy-4-(trifluoromethyl)phenyl]boronic acid (240 mg), potassium carbonate (160 mg), water (0.3 mL), 1,4-dioxane (3 mL) and RuPhos Pd G3 (48 mg) were mixed and stirred under microwave irradiation at 100° C. for 2 hours in an argon atmosphere. The reaction mixture was allowed to cool to room temperature, and water was then added, followed by extraction with chloroform. The organic layer was dried over anhydrous magnesium sulfate. The solution was concentrated under reduced pressure, and the obtained residue was then purified by silica gel column chromatography (chloroform/methanol). To the obtained purified product was added diisopropyl ether, followed by trituration. The precipitated solid was collected by filtration to give 2-(6-{[(1R,2R)-2-hydroxycyclohexyl]amino}-4,5-dimethylpyridazin-3-yl)-5-(trifluoromethyl)phenol (70 mg) as a solid.

Example 68

1-[(6-chloro-4,5-dimethylpyridazine-3-yl)amino]-2-methylpropan-2-ol (170 mg), [2-hydroxy-4-(trifluoromethyl)phenyl]boronic acid (230 mg), potassium carbonate (200 mg), water (0.34 mL), 1,4-dioxane (3.4 mL) and RuPhos Pd G3 (60 mg) were mixed and stirred at 100° C. for 5 hours in an argon atmosphere. The reaction mixture was allowed to cool to room temperature, and water was then added, followed by extraction with chloroform. The organic layer was concentrated under reduced pressure, and the obtained residue was then purified by silica gel column chromatography (chloroform/methanol). To the obtained purified product was added ethyl acetate, followed by trituration. The precipitated solid was collected by filtration to give 2-{6-[(2-hydroxy-2-methylpropyl) amino]-4,5-dimethylpyridazine-3-yl}-5-(trifluoromethyl)phenol (72 mg) as a solid.

Example 70

2-(6-chloro-4,5-dimethylpyridazine-3-yl)-5-(trifluoromethyl)phenol (110 mg), 3-amino-1-propanol (0.17 mL) and DIPEA (0.14 mL) were mixed and stirred overnight at 120° C. in an argon atmosphere. Ethanol was added to the reaction mixture, which was concentrated under reduced pressure. Water was added to the obtained residue, which was then washed successively with chloroform and ethyl acetate. The aqueous layer was concentrated under reduced pressure, and ethanol and toluene were added to the obtained residue, which was concentrated under reduced pressure. Ethanol, toluene and Celite were added to the obtained residue, and the mixture was concentrated under reduced pressure. The obtained residue was purified by silica gel column chromatography (chloroform/methanol) to give 2-{6-[(3-hydroxypropyl) amino]-4,5-dimethylpyridazine-3-yl}-5-(trifluoromethyl)phenol (120 mg) as an oily material.

Example 76

2-{6-[(3-hydroxy-2-methylpropyl)amino]-4,5-dimethylpyridazine-3-yl}-5-(trifluoromethyl)phenol (430 mg) was separated by chiral column chromatography (CHIRALPAK IA). The later eluted fraction was concentrated under reduced pressure, and ethyl acetate was added, followed by trituration. The precipitated solid was collected by filtration to give 2-(6-{[(2R)-3-hydroxy-2-methylpropyl]amino}-4,5-dimethylpyridazine-3-yl)-5-(trifluoromethyl)phenol (160 mg) as a solid.

Example 80

To a mixture of 2-(6-{[(1R,2R)-2-hydroxycyclohexyl]amino}-4,5-dimethylpyridazine-3-yl)-5-(trifluoromethyl)phenol (3.5 g) and methanol (70 mL), 2M hydrogen chloride methanol solution (9.2 mL) was added at room temperature and stirred at the same temperature for 10 minutes. The reaction mixture was concentrated under reduced pressure. Acetonitrile (70 mL) was added at room temperature, and the mixture was stirred at 50° C. for 3 days. The precipitated solid was collected by filtration to give 2-(6-{[(1R,2R)-2-hydroxycyclohexyl]amino}-4,5-dimethylpyridazine-3-yl)-5-(trifluoromethyl) phenol monohydrochloride (3.8 g) as a solid.

Compounds of Production Examples and Examples shown in the tables below were produced in the same manner as in Production Examples or Examples above.

TABLE 3
| PEx | Str |
| --- | --- |
| 1 | 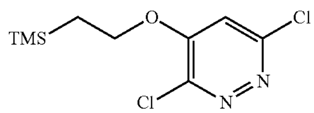 [SMILES: C[Si](C)(C)CCOc1cc(Cl)nnc1Cl] |
| 2 | 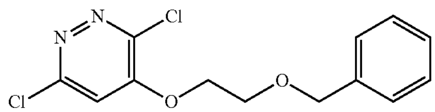 [SMILES: Clc1cc(OCCOCc2ccccc2)c(Cl)nn1] |
| 3 | 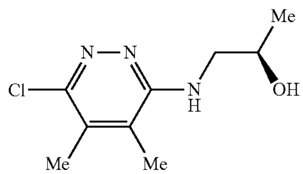 [SMILES: Cc1c(Cl)nnc(NC[C@@H](C)O)c1C] |
| 4(1) | 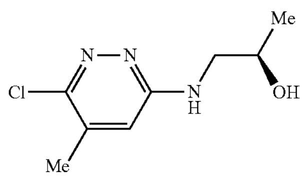 [SMILES: Cc1cc(NC[C@@H](C)O)nnc1Cl] |
| 4(2) | 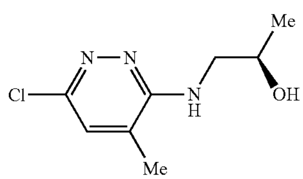 [SMILES: Cc1cc(Cl)nnc1NC[C@@H](C)O] |
| 5 | 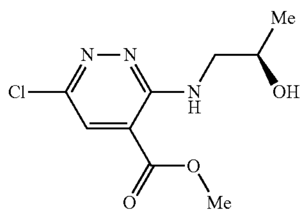 [SMILES: COC(=O)c1cc(Cl)nnc1NC[C@@H](C)O] |
| 6 | 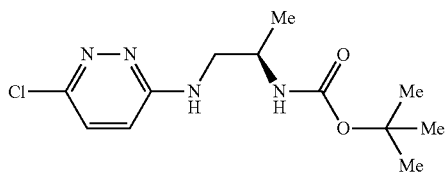 [SMILES: C[C@H](CNc1ccc(Cl)nn1)NC(=O)OC(C)(C)C] |
| 7 | 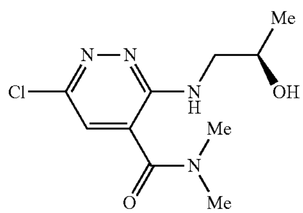 [SMILES: C[C@@H](O)CNc1nnc(Cl)cc1C(=O)N(C)C] |
| 8 | 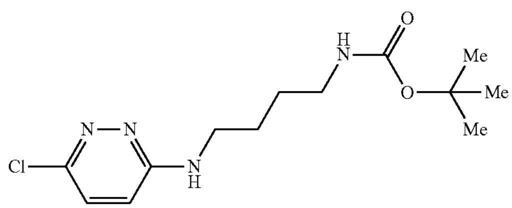 [SMILES: CC(C)(C)OC(=O)NCCCCNc1ccc(Cl)nn1] |

TABLE 3-continued
| PEx | Str |
| --- | --- |
| 9 | 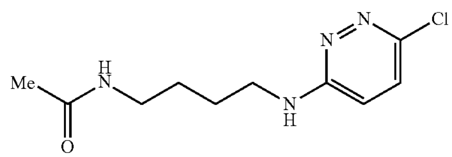 [SMILES: CC(=O)NCCCCNc1ccc(Cl)nn1] |
| 10 | 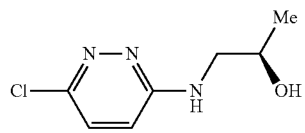 [SMILES: C[C@@H](O)CNc1ccc(Cl)nn1] |
| 11 | 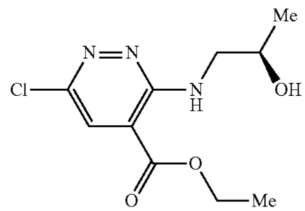 [SMILES: CCOC(=O)c1cc(Cl)nnc1NC[C@@H](C)O] |
| 12 | 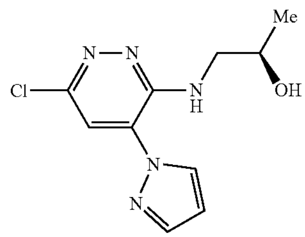 [SMILES: C[C@@H](O)CNc1nnc(Cl)cc1-n1cccn1] |
| 13 | 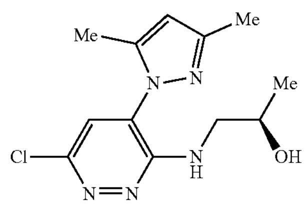 [SMILES: Cc1cc(C)n(-c2cc(Cl)nnc2NC[C@@H](C)O)n1] |
| 14(1) | 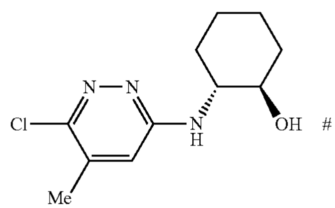 # |
| 14(2) | 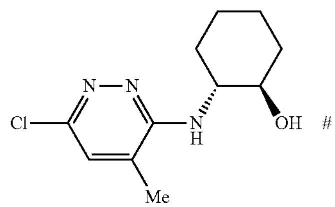 # |

TABLE 3-continued
| PEx | Str |
|---|---|
| 15 | 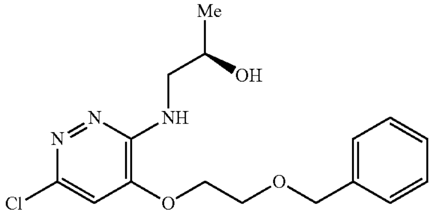 [SMILES: C[C@@H](O)CNc1nnc(Cl)cc1OCCOCc1ccccc1] |
| 16 | 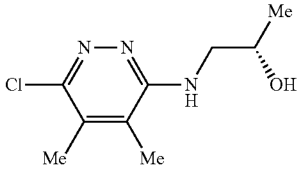 [SMILES: Cc1c(Cl)nnc(NC[C@H](C)O)c1C] |
| 17 | 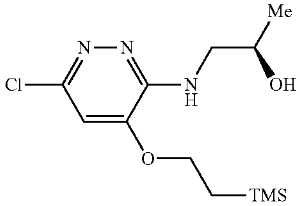 [SMILES: C[C@@H](O)CNc1nnc(Cl)cc1OCC[Si](C)(C)C] |
| 18(1) | 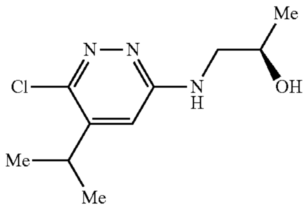 [SMILES: CC(C)c1cc(NC[C@@H](C)O)nnc1Cl] |
| 18(2) | 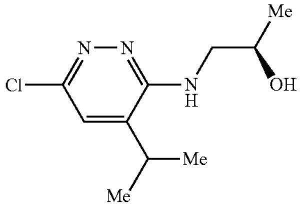 [SMILES: CC(C)c1cc(Cl)nnc1NC[C@@H](C)O] |
| 19(1) | 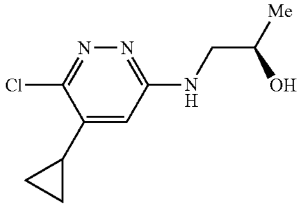 [SMILES: C[C@@H](O)CNc1cc(C2CC2)c(Cl)nn1] |
| 19(2) | 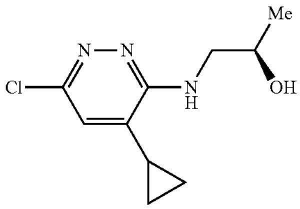 [SMILES: C[C@@H](O)CNc1nnc(Cl)cc1C1CC1] |

TABLE 3-continued
| PEx | Str |
|---|---|
| 20 | 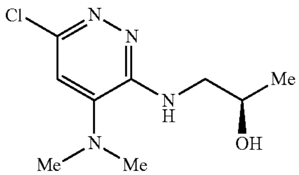 [SMILES: C[C@@H](O)CNc1nnc(Cl)cc1N(C)C] |
| 21 | 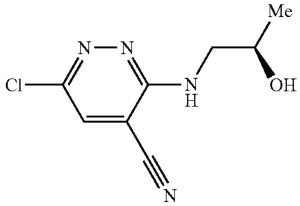 [SMILES: C[C@@H](O)CNc1nnc(Cl)cc1C#N] |
| 22 | 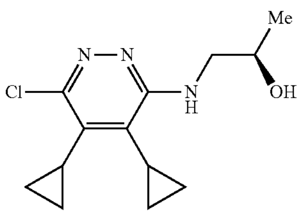 [SMILES: C[C@@H](O)CNc1nnc(Cl)c(C2CC2)c1C1CC1] |
| 23 | 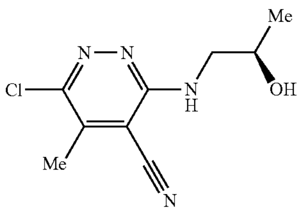 [SMILES: Cc1c(Cl)nnc(NC[C@@H](C)O)c1C#N] |
| 24(1) | 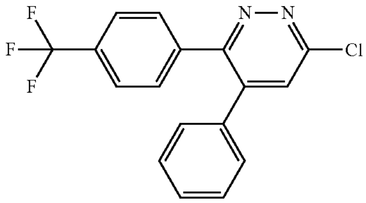 [SMILES: FC(F)(F)c1ccc(-c2nnc(Cl)cc2-c2ccccc2)cc1] |
| 24(2) | 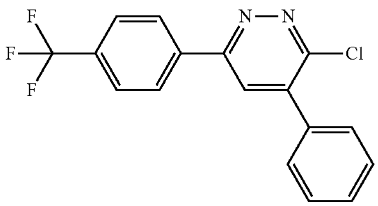 [SMILES: FC(F)(F)c1ccc(-c2cc(-c3ccccc3)c(Cl)nn2)cc1] |
| 25 | 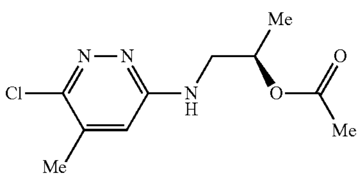 [SMILES: CC(=O)O[C@H](C)CNc1cc(C)c(Cl)nn1] |

TABLE 3-continued
| PEx | Str |
|---|---|
| 26 | 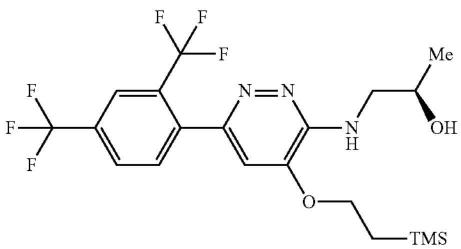 [SMILES: C[C@@H](O)CNc1nnc(-c2ccc(C(F)(F)F)cc2C(F)(F)F)cc1OCC[Si](C)(C)C] |
| 27 | 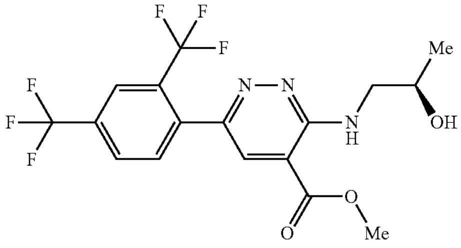 [SMILES: COC(=O)c1cc(-c2ccc(C(F)(F)F)cc2C(F)(F)F)nnc1NC[C@@H](C)O] |
| 28 | 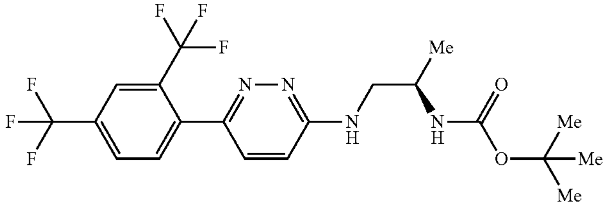 [SMILES: C[C@H](CNc1ccc(-c2ccc(C(F)(F)F)cc2C(F)(F)F)nn1)NC(=O)OC(C)(C)C] |
| 29 | 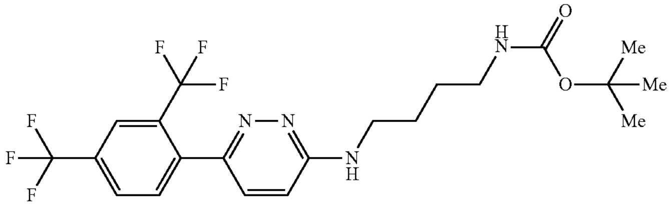 [SMILES: CC(C)(C)OC(=O)NCCCCNc1ccc(-c2ccc(C(F)(F)F)cc2C(F)(F)F)nn1] |
| 30 | 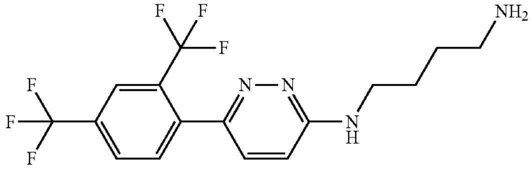 [SMILES: NCCCCNc1ccc(-c2ccc(C(F)(F)F)cc2C(F)(F)F)nn1] |
| 31 | 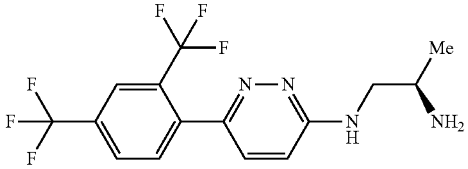 [SMILES: C[C@@H](N)CNc1ccc(-c2ccc(C(F)(F)F)cc2C(F)(F)F)nn1] |
| 32 | 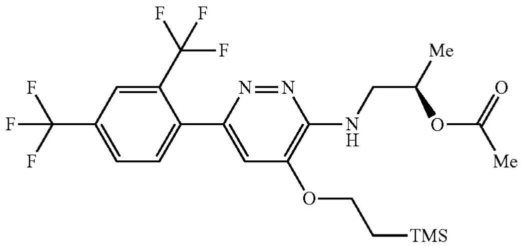 [SMILES: CC(=O)O[C@H](C)CNc1nnc(-c2ccc(C(F)(F)F)cc2C(F)(F)F)cc1OCC[Si](C)(C)C] |

TABLE 3-continued
| PEx | Str |
|---|---|
| 33 | 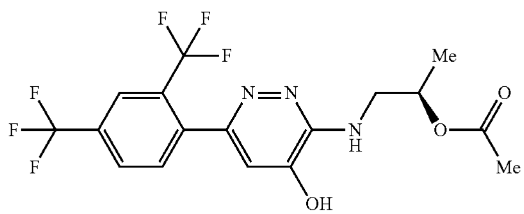 [SMILES: CC(=O)O[C@H](C)CNc1nnc(-c2ccc(C(F)(F)F)cc2C(F)(F)F)cc1O] |
| 34 | 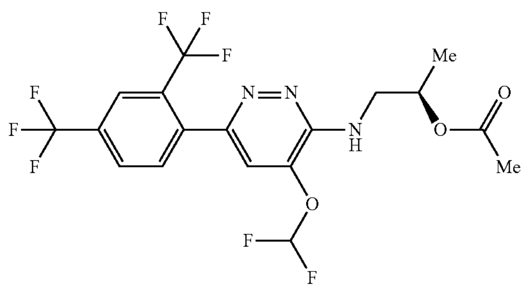 [SMILES: CC(=O)O[C@H](C)CNc1nnc(-c2ccc(C(F)(F)F)cc2C(F)(F)F)cc1OC(F)F] |
| 35 | 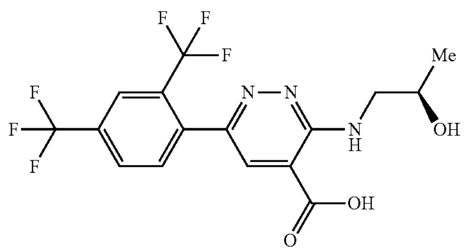 [SMILES: C[C@@H](O)CNc1nnc(-c2ccc(C(F)(F)F)cc2C(F)(F)F)cc1C(=O)O] |
| 36(1) | 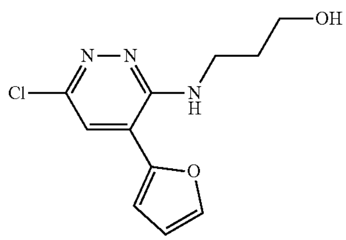 [SMILES: OCCCNc1nnc(Cl)cc1-c1ccco1] |
| 36(2) | 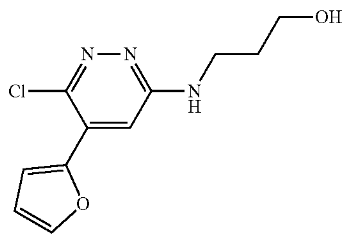 [SMILES: OCCCNc1cc(-c2ccco2)c(Cl)nn1] |
| 37 | 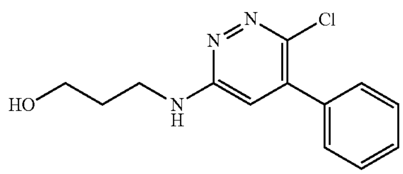 [SMILES: OCCCNc1cc(-c2ccccc2)c(Cl)nn1] |

TABLE 3-continued
| PEx | Str |
|---|---|
| 38 | 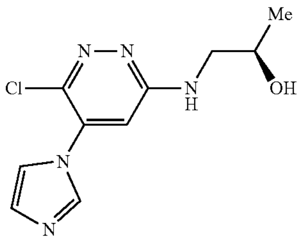 [SMILES: C[C@@H](O)CNc1cc(-n2ccnc2)c(Cl)nn1] |
| 39 | 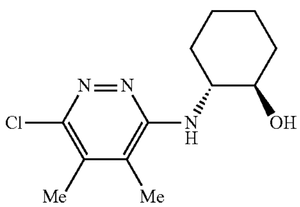 [SMILES: Cc1c(Cl)nnc(N[C@@H]2CCCC[C@H]2O)c1C] |
| 40(1) | 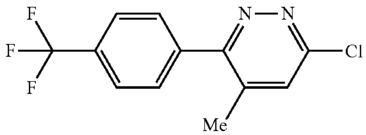 [SMILES: Cc1cc(Cl)nnc1-c1ccc(C(F)(F)F)cc1] |
| 40(2) | 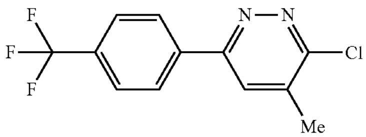 [SMILES: Cc1cc(-c2ccc(C(F)(F)F)cc2)nnc1Cl] |
| 41 | 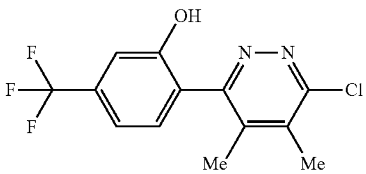 [SMILES: Cc1c(Cl)nnc(-c2ccc(C(F)(F)F)cc2O)c1C] |
| 42 | 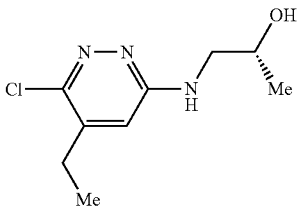 [SMILES: CCc1cc(NC[C@@H](C)O)nnc1Cl] |
| 43 | 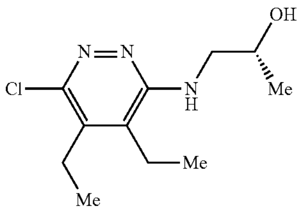 [SMILES: CCc1c(Cl)nnc(NC[C@@H](C)O)c1CC] |
| 44 | 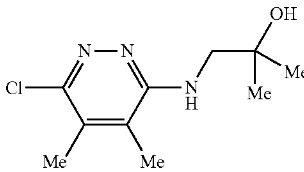 |

TABLE 3-continued
| PEx | Str |
|---|---|
| 45 | 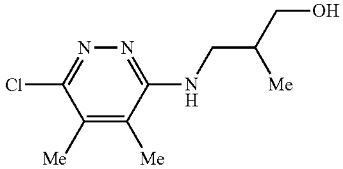 [SMILES: Cc1c(Cl)nnc(NCC(C)CO)c1C] |
| 46 | 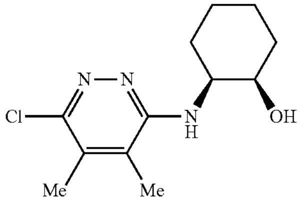 [SMILES: Cc1c(Cl)nnc(N[C@H]2CCCC[C@H]2O)c1C] |
| 47 | 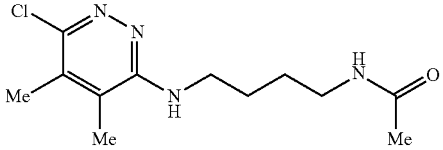 [SMILES: CC(=O)NCCCCNc1nnc(Cl)c(C)c1C] |
| 48 | 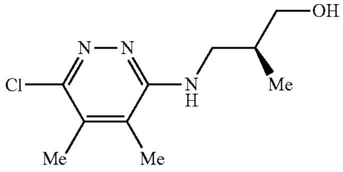 [SMILES: Cc1c(Cl)nnc(NC[C@H](C)CO)c1C] |
| 49 | 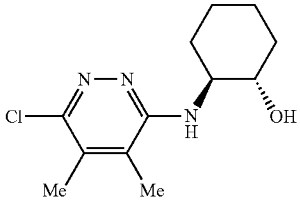 [SMILES: Cc1c(Cl)nnc(N[C@H]2CCCC[C@@H]2O)c1C] |
TABLE 4
| Ex | Str |
|---|---|
| 1 | 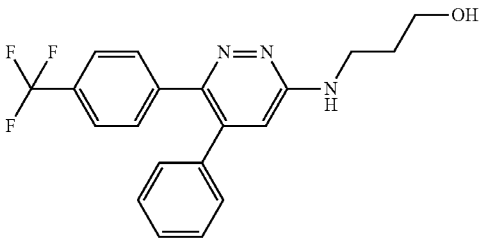 [SMILES: OCCCNc1cc(-c2ccccc2)c(-c2ccc(C(F)(F)F)cc2)nn1] |
| 2 | 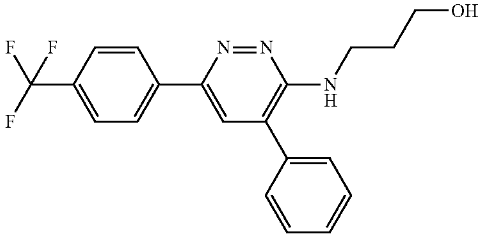 [SMILES: OCCCNc1nnc(-c2ccc(C(F)(F)F)cc2)cc1-c1ccccc1] |
TABLE 4-continued
| Ex | Str |
|---|---|
| 3 | 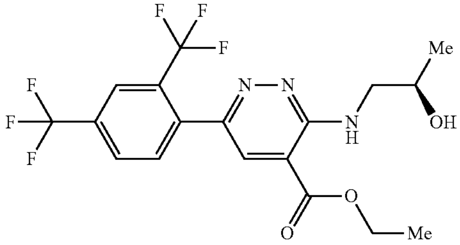 [SMILES: CCOC(=O)c1cc(-c2ccc(C(F)(F)F)cc2C(F)(F)F)nnc1NC[C@@H](C)O] |
| 4 | 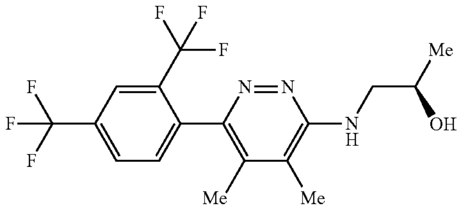 [SMILES: Cc1c(NC[C@@H](C)O)nnc(-c2ccc(C(F)(F)F)cc2C(F)(F)F)c1C] |

TABLE 4-continued
| Ex | Str |
|---|---|
| 5 | 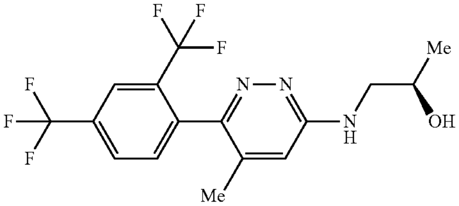 [SMILES: Cc1cc(NC[C@@H](C)O)nnc1-c1ccc(C(F)(F)F)cc1C(F)(F)F] |
| 6 | 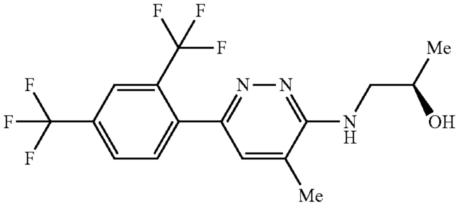 [SMILES: Cc1cc(-c2ccc(C(F)(F)F)cc2C(F)(F)F)nnc1NC[C@@H](C)O] |
| 7 | 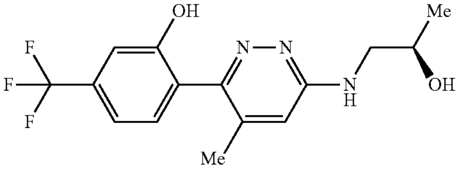 [SMILES: Cc1cc(NC[C@@H](C)O)nnc1-c1ccc(C(F)(F)F)cc1O] |
| 8 | 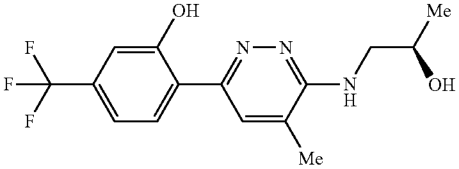 [SMILES: Cc1cc(-c2ccc(C(F)(F)F)cc2O)nnc1NC[C@@H](C)O] |
| 9 | 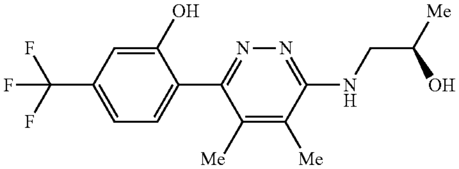 [SMILES: Cc1c(NC[C@@H](C)O)nnc(-c2ccc(C(F)(F)F)cc2O)c1C] |
| 10 | 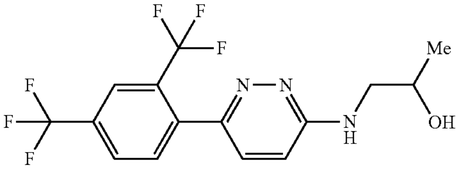 [SMILES: CC(O)CNc1ccc(-c2ccc(C(F)(F)F)cc2C(F)(F)F)nn1] |
| 11 | 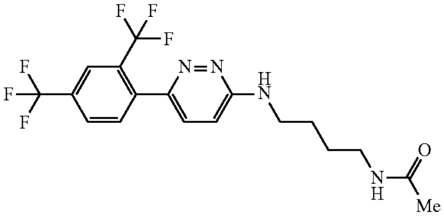 [SMILES: CC(=O)NCCCCNc1ccc(-c2ccc(C(F)(F)F)cc2C(F)(F)F)nn1] |
| 12 | 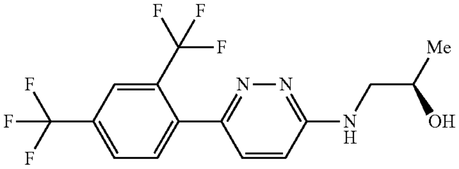 [SMILES: C[C@@H](O)CNc1ccc(-c2ccc(C(F)(F)F)cc2C(F)(F)F)nn1] |
TABLE 4-continued
| Ex | Str |
|---|---|
| 13 | 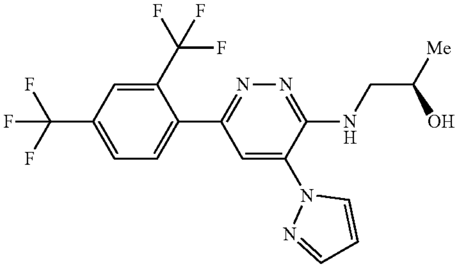 [SMILES: C[C@@H](O)CNc1nnc(-c2ccc(C(F)(F)F)cc2C(F)(F)F)cc1-n1cccn1] |
| 14 | 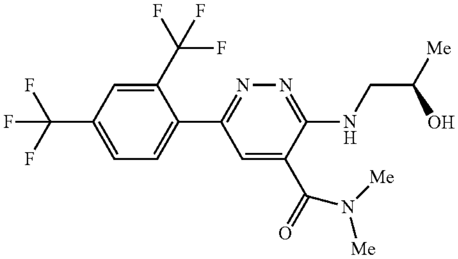 [SMILES: C[C@@H](O)CNc1nnc(-c2ccc(C(F)(F)F)cc2C(F)(F)F)cc1C(=O)N(C)C] |
| 15 | 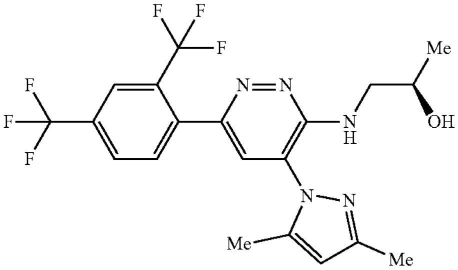 [SMILES: Cc1cc(C)n(-c2cc(-c3ccc(C(F)(F)F)cc3C(F)(F)F)nnc2NC[C@@H](C)O)n1] |
| 16 | 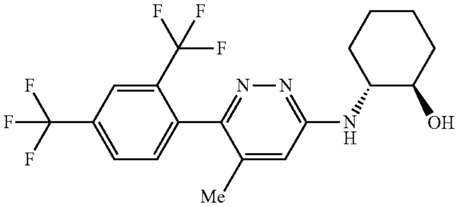 # |
| 17 | 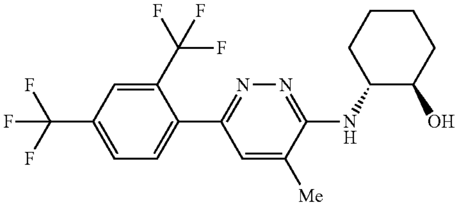 # |
| 18 | 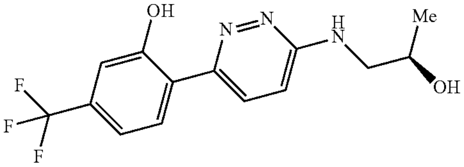 [SMILES: C[C@@H](O)CNc1ccc(-c2ccc(C(F)(F)F)cc2O)nn1] |

TABLE 4-continued
| Ex | Str |
|---|---|
| 19 | 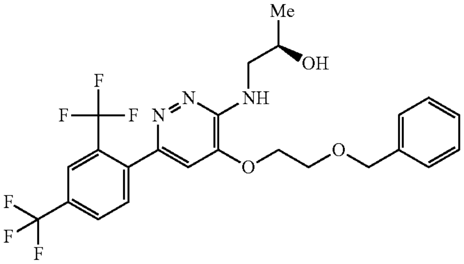 [SMILES: C[C@@H](O)CNc1nnc(-c2ccc(C(F)(F)F)cc2C(F)(F)F)cc1OCCOCc1ccccc1] |
| 20 | 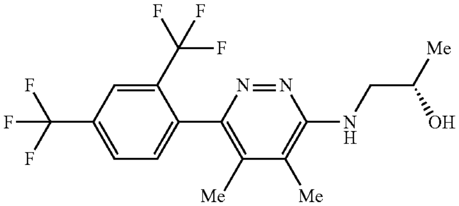 [SMILES: Cc1c(NC[C@H](C)O)nnc(-c2ccc(C(F)(F)F)cc2C(F)(F)F)c1C] |
| 21 | 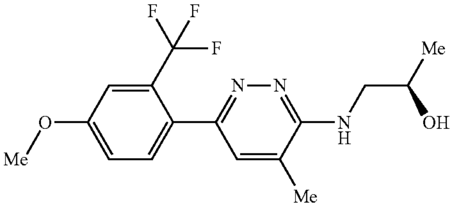 [SMILES: COc1ccc(-c2cc(C)c(NC[C@@H](C)O)nn2)c(C(F)(F)F)c1] |
| 22 | 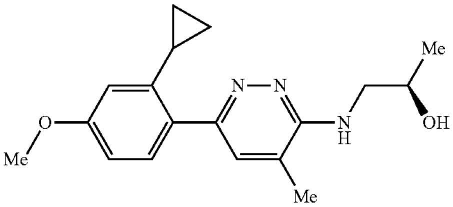 [SMILES: COc1ccc(-c2cc(C)c(NC[C@@H](C)O)nn2)c(C2CC2)c1] |
| 23 | 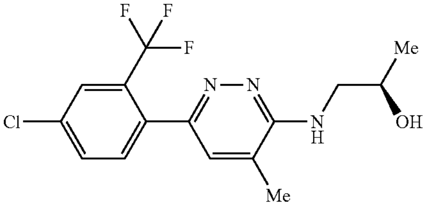 [SMILES: Cc1cc(-c2ccc(Cl)cc2C(F)(F)F)nnc1NC[C@@H](C)O] |
| 24 | 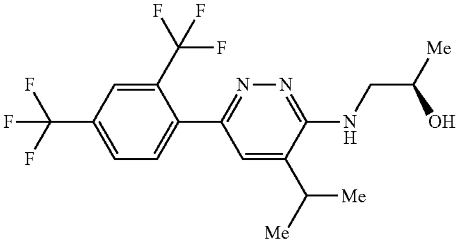 [SMILES: CC(C)c1cc(-c2ccc(C(F)(F)F)cc2C(F)(F)F)nnc1NC[C@@H](C)O] |
| 25 | 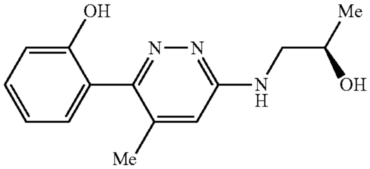 [SMILES: Cc1cc(NC[C@@H](C)O)nnc1-c1ccccc1O] |
TABLE 4-continued
| Ex | Str |
|---|---|
| 26 | 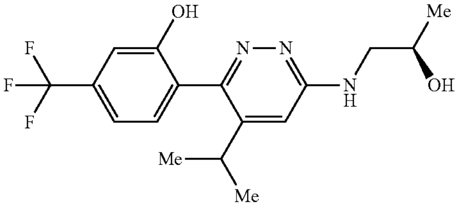 [SMILES: CC(C)c1cc(NC[C@@H](C)O)nnc1-c1ccc(C(F)(F)F)cc1O] |
| 27 | 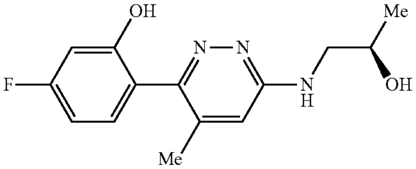 [SMILES: Cc1cc(NC[C@@H](C)O)nnc1-c1ccc(F)cc1O] |
| 28 | 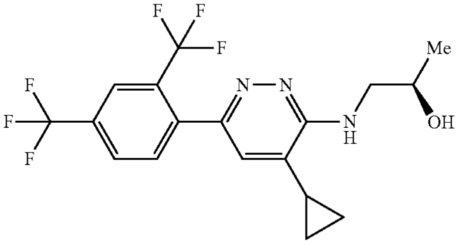 [SMILES: C[C@@H](O)CNc1nnc(-c2ccc(C(F)(F)F)cc2C(F)(F)F)cc1C1CC1] |
| 29 | 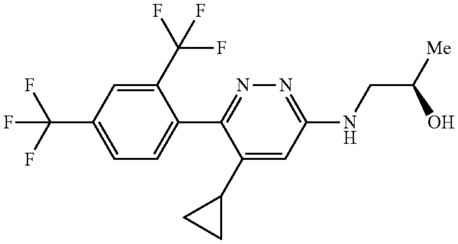 [SMILES: C[C@@H](O)CNc1cc(C2CC2)c(-c2ccc(C(F)(F)F)cc2C(F)(F)F)nn1] |
| 30 | 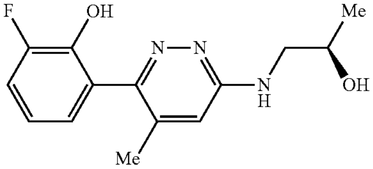 [SMILES: Cc1cc(NC[C@@H](C)O)nnc1-c1cccc(F)c1O] |
| 31 | 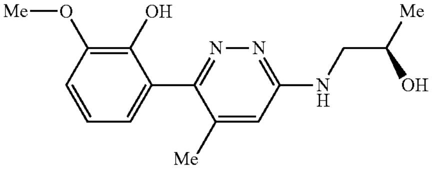 [SMILES: COc1cccc(-c2nnc(NC[C@@H](C)O)cc2C)c1O] |
| 32 | 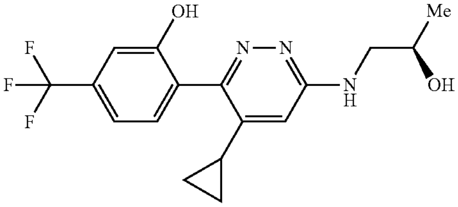 [SMILES: C[C@@H](O)CNc1cc(C2CC2)c(-c2ccc(C(F)(F)F)cc2O)nn1] |

TABLE 4-continued
| Ex | Str |
|---|---|
| 33 | 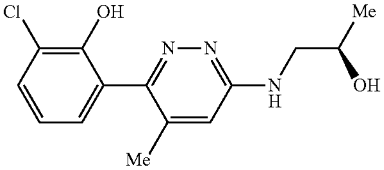 [SMILES: Cc1cc(NC[C@@H](C)O)nnc1-c1cccc(Cl)c1O] |
| 34 | 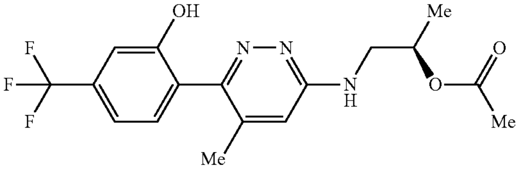 [SMILES: CC(=O)O[C@H](C)CNc1cc(C)c(-c2ccc(C(F)(F)F)cc2O)nn1] |
| 35 | 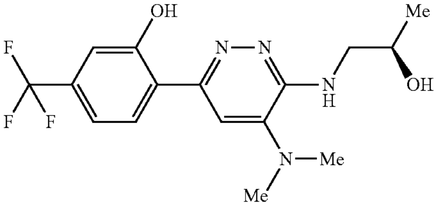 [SMILES: C[C@@H](O)CNc1nnc(-c2ccc(C(F)(F)F)cc2O)cc1N(C)C] |
| 36 | 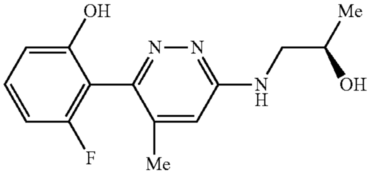 [SMILES: Cc1cc(NC[C@@H](C)O)nnc1-c1c(O)cccc1F] |
| 37 | 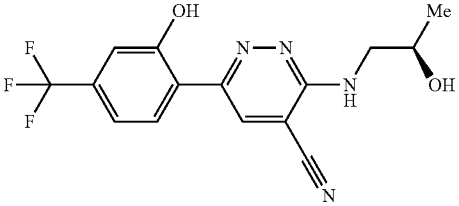 [SMILES: C[C@@H](O)CNc1nnc(-c2ccc(C(F)(F)F)cc2O)cc1C#N] |
| 38 | 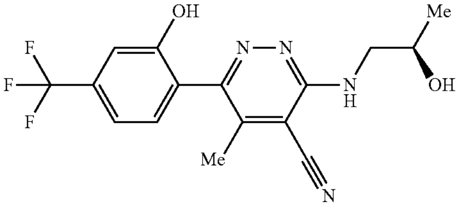 [SMILES: Cc1c(-c2ccc(C(F)(F)F)cc2O)nnc(NC[C@@H](C)O)c1C#N] |
| 39 | 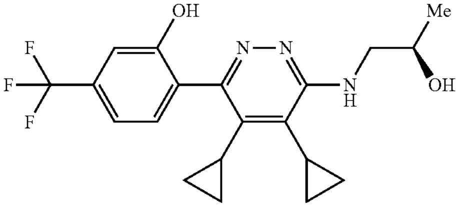 [SMILES: C[C@@H](O)CNc1nnc(-c2ccc(C(F)(F)F)cc2O)c(C2CC2)c1C1CC1] |
TABLE 4-continued
| Ex | Str |
|---|---|
| 40 | 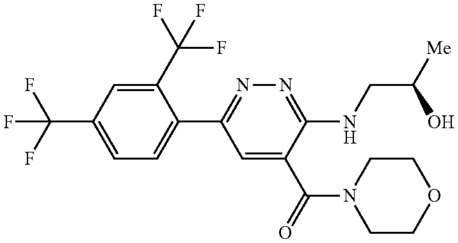 [SMILES: C[C@@H](O)CNc1nnc(-c2ccc(C(F)(F)F)cc2C(F)(F)F)cc1C(=O)N1CCOCC1] |
| 41 | 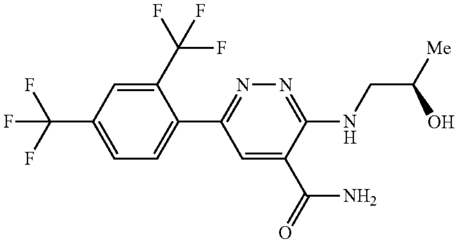 |
| 42 | 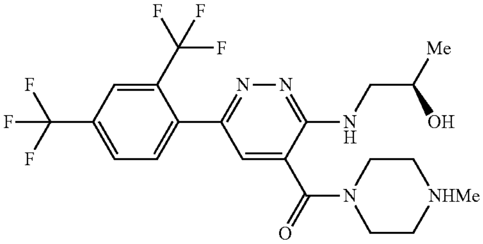 |
| 43 | 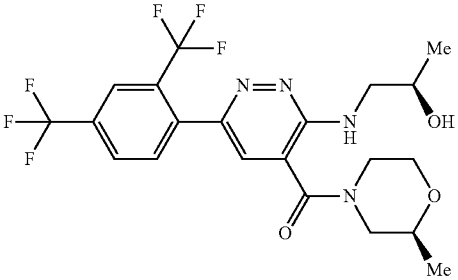 [SMILES: C[C@@H](O)CNc1nnc(-c2ccc(C(F)(F)F)cc2C(F)(F)F)cc1C(=O)N1CCO[C@@H](C)C1] |
| 44 | 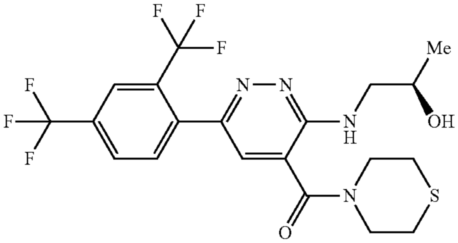 [SMILES: C[C@@H](O)CNc1nnc(-c2ccc(C(F)(F)F)cc2C(F)(F)F)cc1C(=O)N1CCSCC1] |
| 45 | 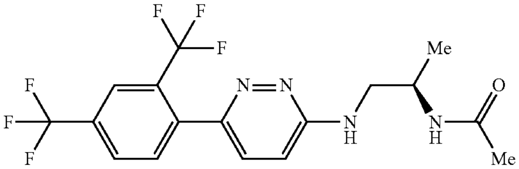 [SMILES: CC(=O)N[C@H](C)CNc1ccc(-c2ccc(C(F)(F)F)cc2C(F)(F)F)nn1] |

TABLE 4-continued
| Ex | Str |
|---|---|
| 46 | 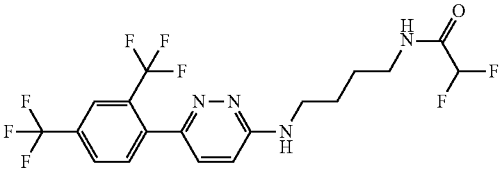 [SMILES: O=C(NCCCCNc1ccc(-c2ccc(C(F)(F)F)cc2C(F)(F)F)nn1)C(F)F] |
| 47 | 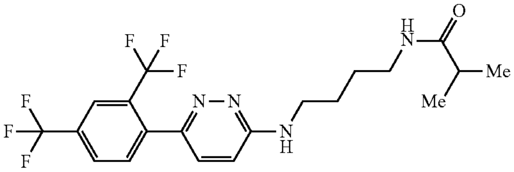 [SMILES: CC(C)C(=O)NCCCCNc1ccc(-c2ccc(C(F)(F)F)cc2C(F)(F)F)nn1] |
| 48 | 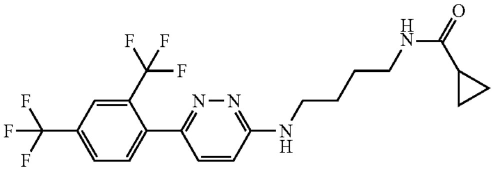 [SMILES: O=C(NCCCCNc1ccc(-c2ccc(C(F)(F)F)cc2C(F)(F)F)nn1)C1CC1] |
| 49 | 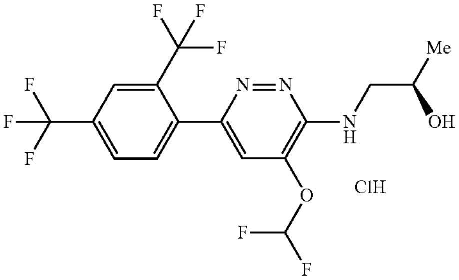 [SMILES: C[C@@H](O)CNc1nnc(-c2ccc(C(F)(F)F)cc2C(F)(F)F)cc1OC(F)F ; Cl] |
| 50 | 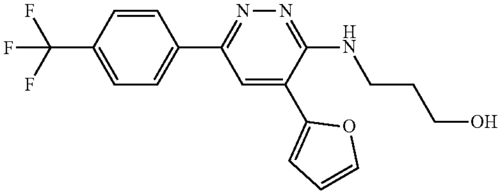 [SMILES: OCCCNc1nnc(-c2ccc(C(F)(F)F)cc2)cc1-c1ccco1] |
| 51 | 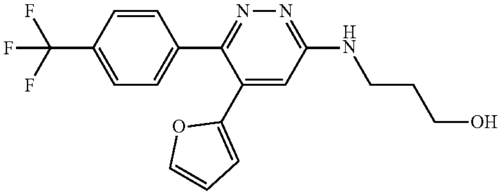 [SMILES: OCCCNc1cc(-c2ccco2)c(-c2ccc(C(F)(F)F)cc2)nn1] |
| 52 | 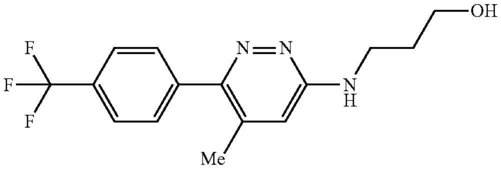 [SMILES: Cc1cc(NCCCO)nnc1-c1ccc(C(F)(F)F)cc1] |
| 53 | 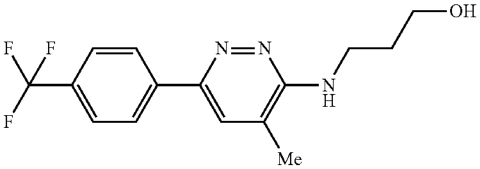 [SMILES: Cc1cc(-c2ccc(C(F)(F)F)cc2)nnc1NCCCO] |
TABLE 4-continued
| Ex | Str |
|---|---|
| 54 | 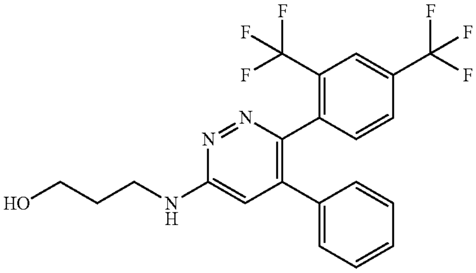 [SMILES: OCCCNc1cc(-c2ccccc2)c(-c2ccc(C(F)(F)F)cc2C(F)(F)F)nn1] |
| 55 | 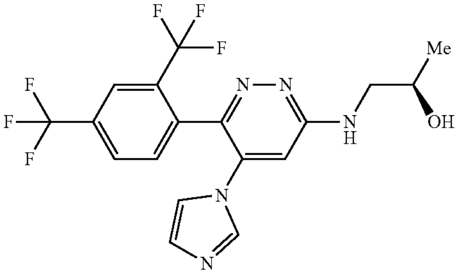 [SMILES: C[C@@H](O)CNc1cc(-n2ccnc2)c(-c2ccc(C(F)(F)F)cc2C(F)(F)F)nn1] |
| 56 | 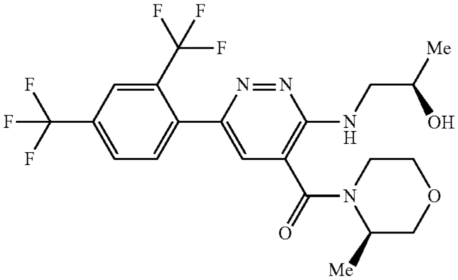 [SMILES: C[C@@H]1COCCN1C(=O)c1cc(-c2ccc(C(F)(F)F)cc2C(F)(F)F)nnc1NC[C@@H](C)O] |
| 57 | 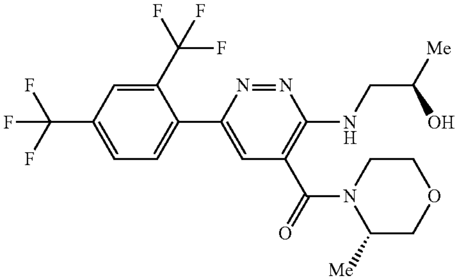 [SMILES: C[C@@H](O)CNc1nnc(-c2ccc(C(F)(F)F)cc2C(F)(F)F)cc1C(=O)N1CCOC[C@@H]1C] |
| 58 | 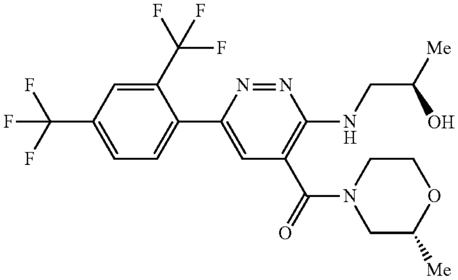 [SMILES: C[C@@H]1CN(C(=O)c2cc(-c3ccc(C(F)(F)F)cc3C(F)(F)F)nnc2NC[C@@H](C)O)CCO1] |

TABLE 4-continued
| Ex | Str |
| --- | --- |
| 59 | 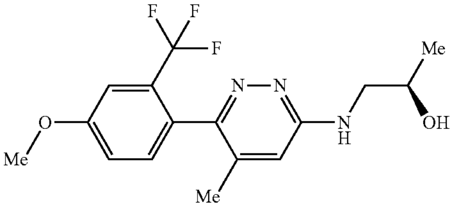 [SMILES: COc1ccc(-c2nnc(NC[C@@H](C)O)cc2C)c(C(F)(F)F)c1] |
| 60 | 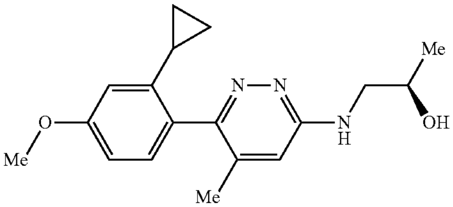 [SMILES: COc1ccc(-c2nnc(NC[C@@H](C)O)cc2C)c(C2CC2)c1] |
| 61 | 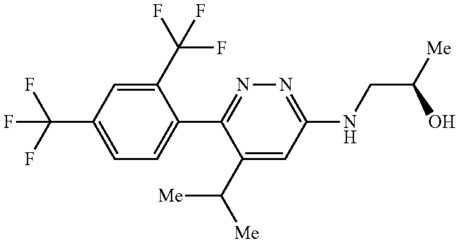 [SMILES: CC(C)c1cc(NC[C@@H](C)O)nnc1-c1ccc(C(F)(F)F)cc1C(F)(F)F] |
| 62 | 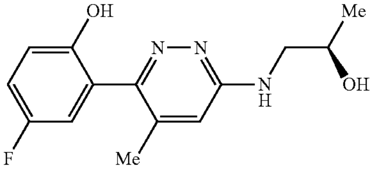 [SMILES: Cc1cc(NC[C@@H](C)O)nnc1-c1cc(F)ccc1O] |
| 63 | 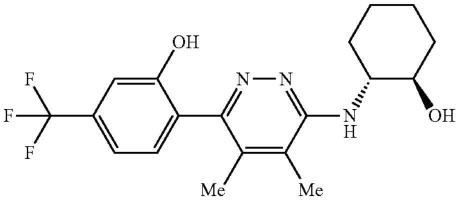 [SMILES: Cc1c(N[C@@H]2CCCC[C@H]2O)nnc(-c2ccc(C(F)(F)F)cc2O)c1C] |
| 64 | 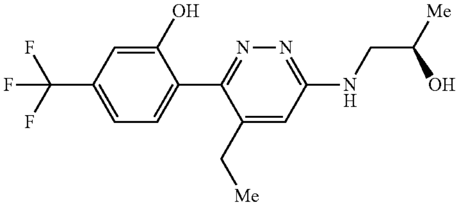 [SMILES: CCc1cc(NC[C@@H](C)O)nnc1-c1ccc(C(F)(F)F)cc1O] |
| 65 | 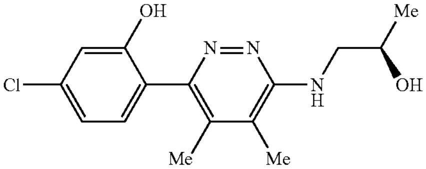 [SMILES: Cc1c(NC[C@@H](C)O)nnc(-c2ccc(Cl)cc2O)c1C] |
| 66 | 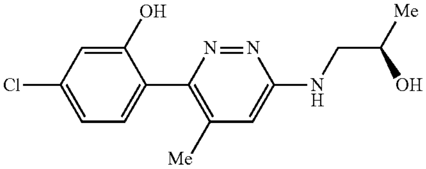 [SMILES: Cc1cc(NC[C@@H](C)O)nnc1-c1ccc(Cl)cc1O] |
| 67 | 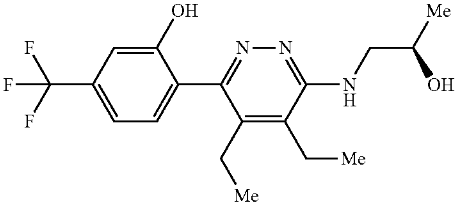 [SMILES: CCc1c(NC[C@@H](C)O)nnc(-c2ccc(C(F)(F)F)cc2O)c1CC] |
| 68 | 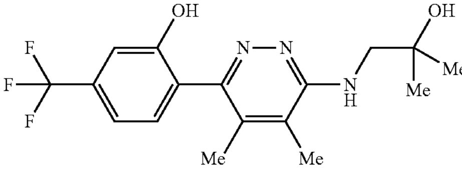 [SMILES: Cc1c(NCC(C)(C)O)nnc(-c2ccc(C(F)(F)F)cc2O)c1C] |
| 69 | 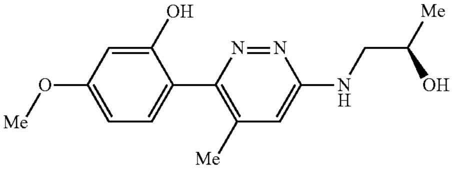 [SMILES: COc1ccc(-c2nnc(NC[C@@H](C)O)cc2C)c(O)c1] |
| 70 | 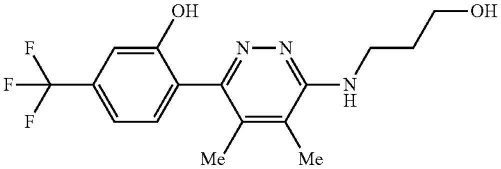 [SMILES: Cc1c(NCCCO)nnc(-c2ccc(C(F)(F)F)cc2O)c1C] |
| 71 | 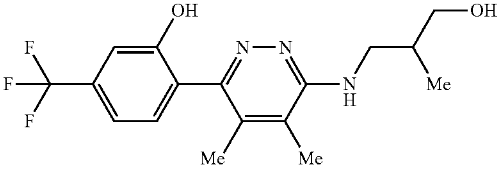 [SMILES: Cc1c(NCC(C)CO)nnc(-c2ccc(C(F)(F)F)cc2O)c1C] |
| 72 | 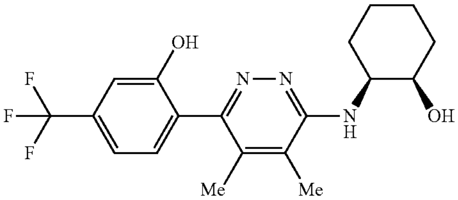 [SMILES: Cc1c(N[C@H]2CCCC[C@H]2O)nnc(-c2ccc(C(F)(F)F)cc2O)c1C] |
| 73 | 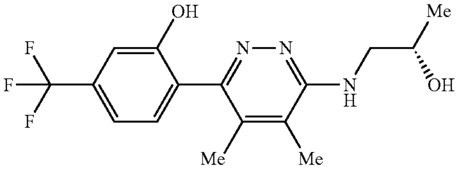 [SMILES: Cc1c(NC[C@H](C)O)nnc(-c2ccc(C(F)(F)F)cc2O)c1C] |

TABLE 4-continued

| Ex | Str |
|---|---|
| 74 | 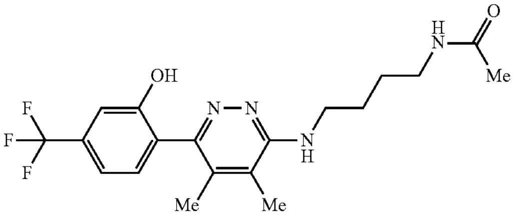 [SMILES: CC(=O)NCCCCNc1nnc(-c2ccc(C(F)(F)F)cc2O)c(C)c1C] |
| 75 | 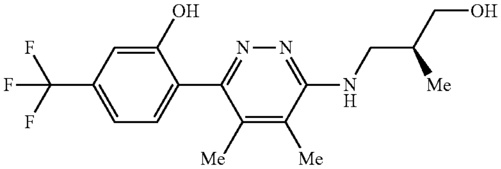 [SMILES: Cc1c(NC[C@H](C)CO)nnc(-c2ccc(C(F)(F)F)cc2O)c1C] |
| 76 | 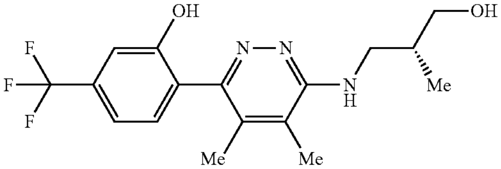 [SMILES: Cc1c(NC[C@@H](C)CO)nnc(-c2ccc(C(F)(F)F)cc2O)c1C] |
| 77 | 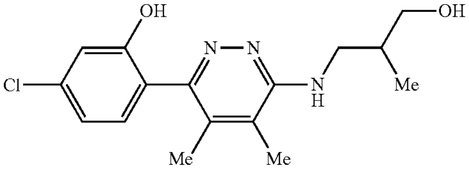 [SMILES: Cc1c(NCC(C)CO)nnc(-c2ccc(Cl)cc2O)c1C] |
| 78 | 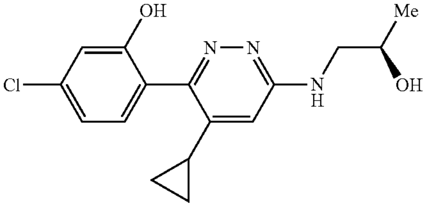 [SMILES: C[C@@H](O)CNc1cc(C2CC2)c(-c2ccc(Cl)cc2O)nn1] |
| 79 | 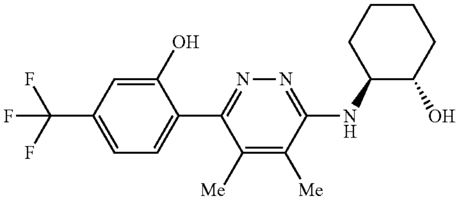 [SMILES: Cc1c(N[C@H]2CCCC[C@@H]2O)nnc(-c2ccc(C(F)(F)F)cc2O)c1C] |

TABLE 4-continued

| Ex | Str |
|---|---|
| 80 | 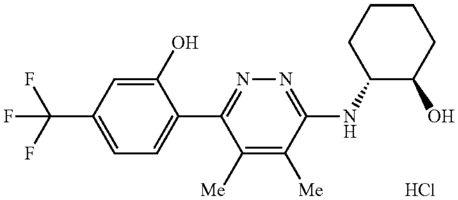 [SMILES: Cc1c(N[C@@H]2CCCC[C@H]2O)nnc(-c2ccc(C(F)(F)F)cc2O)c1C ; Cl] HCl |

TABLE 5

| PEx | PSyn | DAT |
|---|---|---|
| 1 | — | ESI+; 287, 289, 291 [M + Na]+ |
| 2 | — | ESI+; 299, 301 |
| 3 | — | ESI+; 216, 218 |
| 4(1) | — | ESI+; 202, 204 |
| 4(2) | — | ESI+; 202, 204 |
| 5 | 4 | API-ES+; 246 |
| 6 | 4 | ESI+; 287 |
| 7 | 4 | ESI+; 259 |
| 8 | 4 | ESI+; 301 |
| 9 | 4 | ESI+; 243, 245 |
| 10 | 4 | APCI/ESI+; 188 |
| 11 | 3 | ESI+; 260, 262 |
| 12 | 4 | ESI+; 254, 256 |
| 13 | 4 | ESI+; 282, 284 |
| 14(1) | 4 | ESI+; 242, 244 |
| 14(2) | 4 | ESI+; 242, 244 |
| 15 | 4 | ESI+; 338, 340 |
| 16 | 4 | ESI+; 216, 218 |
| 17 | 4 | ESI+; 304, 306 |
| 18(1) | 4 | ESI+; 230, 232 |
| 18(2) | 4 | ESI+; 230, 232 |
| 19(1) | 4 | ESI+; 228, 230 |
| 19(2) | 4 | ESI+; 228, 230 |
| 20 | 3 | ESI+; 231, 233 |
| 21 | 4 | ESI+; 213, 215 |
| 22 | 4 | ESI+; 268, 270 |
| 23 | 4 | ESI+; 227, 229 |
| 24(1) | — | APCI/ESI+; 335 |
| 24(2) | — | APCI/ESI+; 335 |
| 25 | — | ESI+; 244, 246 |
| 26 | — | ESI+; 482 |
| 27 | 26 | ESI+; 424 |
| 28 | 26 | ESI+; 465 |
| 29 | 26 | ESI+; 479 |
| 30 | — | ESI+; 379 |
| 31 | 30 | ESI+; 365 |
| 32 | — | ESI+; 524 |
| 33 | — | ESI+; 424 |
| 34 | — | ESI+; 474 |
| 35 | — | ESI+; 410 |
| 36(1) | 3 | ESI+; 254, 256 |
| 36(2) | 3 | ESI+; 254, 256 |
| 37 | 4 | ESI+; 264, 266 |
| 38 | 4 | ESI+; 254, 256 |
| 39 | — | ESI+; 256, 258 |
| 40(1) | 24 | APCI/ESI+; 273 |
| 40(2) | 24 | APCI/ESI+; 273 |
| 41 | 24 | ESI+; 303, 305 |
| 42 | 3 | ESI+; 216, 218 |
| 43 | 4 | ESI+; 244, 246 |
| 44 | 4 | ESI+; 230, 232 |
| 45 | 4 | ESI+; 230, 232 |
| 46 | 4 | ESI+; 256, 258 |
| 47 | 4 | ESI+; 271, 273 |
| 48 | 4 | ESI+; 230, 232 |
| 49 | 4 | ESI+; 256, 258 |

TABLE 6

| Ex | Syn | DAT |
|---|---|---|
| 1 | — | APCI/ESI+; 374 |
| 2 | 1 | APCI/ESI+; 374 |
| 3 | — | ESI+; 438<br>$^1$H NMR (400 MHz, DMSO-$d_6$) δ ppm 1.17 (3 H, d, J = 6.2 Hz) 1.32 (3 H, t, J = 7.1 Hz) 3.44 (1 H, ddd, J = 13.2, 7.5, 4.6 Hz) 3.78 (1 H, ddd, J = 13.2, 6.1, 4.1 Hz) 3.90-4.00 (1 H, m) 4.36 (2 H, q, J = 7.1 Hz) 4.98 (1 H, d, J = 4.9 Hz) 7.87-7.92 (1 H, m) 7.94 (1 H, s) 7.96-8.02 (1 H, m) 8.18-8.23 (2 H, m) |
| 4 | — | ESI+; 394<br>$^1$H NMR (500 MHz, DMSO-$d_6$) δ ppm 1.11 (3 H, d, J = 6.3 Hz) 1.87 (3 H, s) 2.10 (3 H, s) 3.36-3.56 (2 H, m) 3.90-3.99 (1 H, m) 4.83-4.91 (1 H, m) 6.18-6.25 (1 H, m) 7.68 (1 H, d, J = 7.8 Hz) 8.12-8.19 (2 H, m) |
| 5 | — | ESI+; 380<br>$^1$H NMR (500 MHz, DMSO-$d_6$) δ ppm 1.12 (3 H, d, J = 6.3 Hz) 1.89 (3 H, d, J = 0.8 Hz) 3.22-3.40 (2 H, m) 3.81-3.90 (1 H, m) 4.80 (1 H, d, J = 4.7 Hz) 6.81 (1 H, d, J = 1.1 Hz) 6.89 (1 H, t, J = 5.7 Hz) 7.73 (1 H, d, J = 8.0 Hz) 8.14-8.20 (2 H, m) |
| 6 | — | ESI+; 380<br>$^1$H NMR (500 MHz, DMSO-$d_6$) δ ppm 1.12 (3 H, d, J = 6.3 Hz) 2.17 (3 H, d, J = 0.8 Hz) 3.37-3.44 (1 H, m) 3.46-3.54 (1 H, m) 3.92-4.01 (1 H, m) 4.86 (1 H, d, J = 4.6 Hz) 6.42 (1 H, t, J = 5.7 Hz) 7.33 (1 H, s) 7.78-7.82 (1 H, m) 8.13-8.18 (2 H, m) |
| 7 | — | ESI+; 328<br>$^1$H NMR (500 MHz, DMSO-$d_6$) δ ppm 1.11 (3 H, d, J = 6.3 Hz) 2.02 (3 H, d, J = 0.9 Hz) 3.23-3.38 (2 H, m) 3.81-3.90 (1 H, m) 4.82 (1 H, d, J = 4.6 Hz) 6.74 (1 H, d, J = 0.9 Hz) 6.76 (1 H, t, J = 5.8 Hz) 7.18-7.21 (1 H, m) 7.21-7.24 (1 H, m) 7.39 (1 H, d, J = 7.6 Hz) 10.46 (1 H, br s) |
| 8 | — | ESI+; 328<br>$^1$H NMR (500 MHz, DMSO-$d_6$) δ ppm 1.12 (3 H, d, J = 6.3 Hz) 2.25 (3 H, d, J = 0.8 Hz) 3.32-3.51 (2 H, m) 3.92-4.01 (1 H, m) 4.80 (1 H, d, J = 4.7 Hz) 6.73 (1 H, t, J = 5.7 Hz) 7.19-7.25 (2 H, m) 8.08 (1 H, d, J = 8.3 Hz) 8.14 (1 H, d, J = 0.8 Hz) 14.60 (1 H, s) |
| 9 | — | ESI+; 342<br>$^1$H NMR (500 MHz, DMSO-$d_6$) δ ppm 1.11 (3 H, d, J = 6.3 Hz) 1.98 (3 H, s) 2.08 (3 H, s) 3.33-3.39 (1 H, m) 3.41-3.50 (1 H, m) 3.90-3.99 (1 H, m) 4.94 (1 H, d, J = 4.0 Hz) 6.11 (1 H, t, J = 5.7 Hz) 7.18-7.20 (1 H, m) 7.21-7.24 (1 H, m) 7.37 (1 H, d, J = 7.6 Hz) 10.30 (1 H, s) |
| 10 | 3 | ESI+; 366 |
| 11 | 3 | ESI+; 421<br>$^1$H NMR (500 MHz, DMSO-$d_6$) δ ppm 1.45-1.53 (2 H, m) 1.55-1.64 (2 H, m) 1.79 (3 H, s) 3.04-3.11 (2 H, m) 3.35-3.42 (2 H, m) 6.90 (1 H, d, J = 9.2 Hz) 7.14 (1 H, t, J = 5.5 Hz) 7.41 (1 H, d, J = 9.3 Hz) 7.79-7.86 (2 H, m) 8.14-8.18 (2 H, m) |
| 12 | 3 | ESI+; 366<br>$^1$H NMR (400 MHz, DMSO-$d_6$) δ ppm 1.13 (3 H, d, J = 6.2 Hz) 3.25-3.36 (1 H, m) 3.37-3.46 (1 H, m) 3.82-3.93 (1 H, m) 4.81 (1 H, d, J = 4.9 Hz) 7.00 (1 H, d, J = 9.3 Hz) 7.11 (1 H, t, J = 5.7 Hz) 7.41 (1 H, d, J = 9.3 Hz) 7.81 (1 H, d, J = 8.6 Hz) 8.14-8.18 (2 H, m) |
| 13 | 3 | ESI+; 432<br>$^1$H NMR (500 MHz, DMSO-$d_6$) δ ppm 1.17 (3 H, d, J = 6.1 Hz) 3.44 (1 H, ddd, J = 13.2, 7.4, 4.6 Hz) 3.75 (1 H, ddd, J = 13.2, 6.0, 4.1 Hz) 3.91-4.00 (1 H, m) 4.91 (1 H, d, J = 4.7 Hz) 6.73 (1 H, dd, J = 2.7, 1.9 Hz) 7.95 (1 H, s) 7.98 (1 H, d, J = 7.8 Hz) 8.01 (1 H, d, J = 1.7 Hz) 8.21-8.25 (2 H, m) 8.42-8.48 (1 H, m) 8.71 (1 H, d, J = 2.4 Hz) |
| 14 | 3 | ESI+; 437 |
| 15 | 3 | ESI+; 460<br>1H NMR (500 MHz, CDCl3) δ ppm 1.29 (3 H, d, J = 6.3 Hz) 2.31 (3 H, s) 2.34 (3 H, s) 3.20 (1 H, d, J = 4.1 Hz) 3.52 (1 H, ddd, J = 14.0, 7.9, 5.4 Hz) 3.93 (1 H, ddd, J = 14.0, 6.5, 2.9 Hz) 4.14-4.23 (1 H, m) 6.10 (1 H, s) 7.06 (1 H, t, J = 5.4 Hz) 7.16 (1 H, s) 7.80 (1 H, d, J = 8.1 Hz) 7.92 (1 H, d, J = 8.1 Hz) 8.04 (1 H, s) |
| 16 | 3 | ESI+; 420<br>$^1$H NMR (500 MHz, DMSO-$d_6$) δ ppm 1.12-1.36 (4 H, m) 1.58-1.71 (2 H, m) 1.89 (3 H, d, J = 1.0 Hz) 1.89-1.94 (1 H, m) 2.02-2.10 (1 H, m) 3.35-3.43 (1 H, m) 3.63-3.72 (1 H, m) 4.74 (1 H, d, J = 5.0 Hz) 6.73 (1 H, d, J = 7.3 Hz) 6.78 (1 H, d, J = 0.9 Hz) 7.73 (1 H, d, J = 8.0 Hz) 8.16 (1 H, d, J = 8.1 Hz) 8.18 (1 H, s) |
| 17 | 3 | ESI+; 420<br>$^1$H NMR (500 MHz, DMSO-$d_6$) δ ppm 1.18-1.36 (4 H, m) 1.60-1.74 (2 H, m) 1.90-2.00 (1 H, m) 2.06-2.14 (1 H, m) 2.17 (3 H, d, J = 0.8 Hz) 3.50-3.58 (1 H, m) 3.94-4.03 (1 H, m) 4.73 (1 H, d, J = 4.9 Hz) 5.97 (1 H, d, J = 7.3 Hz) 7.31 (1 H, s) 7.77-7.82 (1 H, m) 8.14-8.18 (2 H, m) |
| 18 | 3 | ESI+; 314<br>$^1$H NMR (500 MHz, DMSO-$d_6$) δ ppm 1.13 (3 H, d, J = 6.3 Hz) 3.27-3.34 (1 H, m) 3.37-3.44 (1 H, m) 3.84-3.92 (1 H, m) 4.81 (1 H, d, J = 4.9 Hz) 7.19 (1 H, d, J = 9.6 Hz) 7.21-7.24 (2 H, m) 7.38 (1 H, t, J = 5.7 Hz) 8.04 (1 H, d, J = 8.3 Hz) 8.17 (1 H, d, J = 9.6 Hz) 14.31 (1 H, s) |

TABLE 6-continued

| Ex | Syn | DAT |
|---|---|---|
| 19 | 3 | ESI+; 516 |
| 20 | 3 | ESI+; 394 |
| 21 | 3 | ESI+; 342<br>$^1$H NMR (500 MHz, DMSO-$d_6$) δ ppm 1.12 (3 H, d, J = 6.3 Hz) 2.14 (3 H, d, J = 0.9 Hz) 3.34-3.40 (1 H, m) 3.45-3.52 (1 H, m) 3.88 (3 H, s) 3.91-4.00 (1 H, m) 4.88 (1 H, d, J = 4.4 Hz) 6.24 (1 H, t, J = 5.7 Hz) 7.19 (1 H, s) 7.28-7.33 (2 H, m) 7.42-7.46 (1 H, m) |
| 22 | 3 | ESI+; 314 |
| 23 | 3 | ESI+; 346, 348<br>$^1$H NMR (500 MHz, DMSO-$d_6$) δ ppm 1.12 (3 H, d, J = 6.3 Hz) 2.15 (3 H, d, J = 0.9 Hz) 3.34-3.41 (1 H, m) 3.45-3.52 (1 H, m) 3.91-4.00 (1 H, m) 4.86 (1 H, d, J = 4.6 Hz) 6.34 (1 H, t, J = 5.7 Hz) 7.26 (1 H, s) 7.56 (1 H, d, J = 8.4 Hz) 7.84 (1 H, dd, J = 8.2, 2.1 Hz) 7.92 (1 H, d, J = 2.1 Hz) |
| 24 | 3 | ESI+; 408 |
| 25 | 3 | ESI+; 260 |
| 26 | 3 | ESI+; 356<br>$^1$H NMR (500 MHz, DMSO-$d_6$) δ ppm 1.04 (6 H, d, J = 6.9 Hz) 1.13 (3 H, d, J = 6.1 Hz) 2.54-2.63 (1 H, m) 3.22-3.42 (2 H, m) 3.81-3.91 (1 H, m) 5.09 (1 H, br s) 6.85-6.93 (2 H, m) 7.19 (1 H, d, J = 1.4 Hz) 7.24 (1 H, dd, J = 7.9, 1.0 Hz) 7.39 (1 H, d, J = 7.6 Hz) 10.31 (1 H, br s) |
| 27 | 3 | ESI+; 278<br>$^1$H NMR (500 MHz, DMSO-$d_6$) δ ppm 1.11 (3 H, d, J = 6.1 Hz) 2.02 (3 H, d, J = 0.8 Hz) 3.22-3.29 (1 H, m) 3.30-3.37 (1 H, m) 3.81-3.89 (1 H, m) 4.83 (1 H, d, J = 4.1 Hz) 6.65-6.73 (4 H, m) 7.16-7.21 (1 H, m) 10.32 (1 H, br s) |
| 28 | 3 | ESI+; 406<br>$^1$H NMR (500 MHz, DMSO-$d_6$) δ ppm 0.65-0.77 (2 H, m) 0.97-1.05 (2 H, m) 1.14 (3 H, d, J = 6.3 Hz) 1.79-1.86 (1 H, m) 3.40-3.48 (1 H, m) 3.50-3.58 (1 H, m) 3.94-4.03 (1 H, m) 4.89 (1 H, d, J = 4.6 Hz) 6.59 (1 H, t, J = 5.7 Hz) 7.09 (1 H, s) 7.81 (1 H, d, J = 8.6 Hz) 8.12-8.16 (2 H, m) |
| 29 | 3 | ESI+; 406<br>$^1$H NMR (500 MHz, DMSO-$d_6$) δ ppm 0.65-0.70 (2 H, m) 0.81-0.87 (2 H, m) 1.11 (3 H, d, J = 6.3 Hz) 1.16-1.26 (1 H, m) 3.20-3.28 (1 H, m) 3.33-3.40 (1 H, m) 3.79-3.87 (1 H, m) 4.79 (1 H, d, J = 4.7 Hz) 6.46 (1 H, s) 6.71 (1 H, t, J = 5.7 Hz) 7.77 (1 H, d, J = 7.8 Hz) 8.17 (1 H, d, J = 8.3 Hz) 8.19 (1 H, s) |
| 30 | 3 | ESI+; 278 |
| 31 | 3 | ESI+; 290<br>$^1$H NMR (500 MHz, DMSO-$d_6$) δ ppm 1.11 (3 H, d, J = 6.3 Hz) 2.00 (3 H, d, J = 0.9 Hz) 3.22-3.30 (1 H, m) 3.31-3.37 (1 H, m) 3.80-3.89 (1 H, m) 3.84 (3 H, s) 4.84 (1 H, d, J = 4.6 Hz) 6.65 (1 H, t, J = 5.8 Hz) 6.71 (1 H, d, J = 0.9 Hz) 6.76 (1 H, dd, J = 7.6, 1.5 Hz) 6.84 (1 H, t, J = 7.7 Hz) 7.00 (1 H, dd, J = 8.1, 1.5 Hz) 8.96 (1 H, s) |
| 32 | 3 | ESI+; 354<br>$^1$H NMR (500 MHz, DMSO-$d_6$) δ ppm 0.60-0.66 (2 H, m) 0.84-0.89 (2 H, m) 1.11 (3 H, d, J = 6.1 Hz) 1.53 (1 H, tt, J = 8.3, 5.1 Hz) 3.21-3.28 (1 H, m) 3.33-3.38 (1 H, m) 3.79-3.87 (1 H, m) 4.84 (1 H, br s) 6.40 (1 H, s) 6.62 (1 H, t, J = 5.7 Hz) 7.20 (1 H, d, J = 1.5 Hz) 7.23 (1 H, dd, J = 8.0, 1.1 Hz) 7.44 (1 H, d, J = 7.5 Hz) 10.42 (1 H, br s) |
| 33 | 3 | ESI+; 294, 296<br>$^1$H NMR (500 MHz, DMSO-$d_6$) δ ppm 1.12 (3 H, d, J = 6.3 Hz) 2.09 (3 H, d, J = 0.9 Hz) 3.24-3.30 (1 H, m) 3.31-3.38 (1 H, m) 3.82-3.90 (1 H, m) 4.82 (1 H, br s) 6.79 (1 H, d, J = 0.9 Hz) 6.85 (1 H, t, J = 5.7 Hz) 6.93 (1 H, t, J = 7.8 Hz) 7.23 (1 H, dd, J = 7.6, 1.7 Hz) 7.42 (1 H, dd, J = 8.0, 1.7 Hz) 10.49 (1 H, brs) |
| 34 | 3 | ESI+; 370<br>$^1$H NMR (500 MHz, DMSO-$d_6$) δ ppm 1.22 (3 H, d, J = 6.4 Hz) 2.00 (3 H, s) 2.04 (3 H, d, J = 0.9 Hz) 3.40-3.47 (1 H, m) 3.57-3.65 (1 H, m) 5.00-5.08 (1 H, m) 6.73-6.76 (1 H, m) 6.98-7.07 (1 H, m) 7.19-7.21 (1 H, m) 7.23 (1 H, dd, J = 7.9, 1.0 Hz) 7.40 (1 H, d, J = 7.5 Hz) 10.46 (1 H, br s) |
| 35 | 3 | ESI+; 357 |
| 36 | 3 | ESI+; 278 |
| 37 | 3 | ESI+; 339<br>$^1$H NMR (500 MHz, DMSO-$d_6$) δ ppm 1.12 (3 H, d, J = 6.3 Hz) 3.42-3.56 (2 H, m) 3.94-4.03 (1 H, m) 4.85 (1 H, d, J = 4.7 Hz) 7.26-7.29 (2 H, m) 7.52 (1 H, t, J = 5.7 Hz) 8.05 (1 H, d, J = 8.1 Hz) 8.60 (1 H, s) 12.22 (1 H, br s) |
| 38 | 3 | ESI+; 353<br>$^1$H NMR (500 MHz, DMSO-$d_6$) δ ppm 1.12 (3 H, d, J = 6.3 Hz) 2.21 (3 H, s) 3.40-3.47 (1 H, m) 3.48-3.56 (1 H, m) 3.91-4.01 (1 H, m) 4.85 (1 H, br s) 7.09 (1 H, t, J = 5.7 Hz) 7.23 (1 H, d, J = 1.4 Hz) 7.27 (1 H, dd, J = 7.9, 1.0 Hz) 7.45 (1 H, d, J = 7.6 Hz) 10.51 (1 H, br s) |
| 39 | 3 | ESI+; 394 |
| 40 | — | ESI+; 479 |

TABLE 6-continued

| Ex | Syn | DAT |
|---|---|---|
| 41 | 40 | ESI+; 409<br>$^1H$ NMR (500 MHz, DMSO-$d_6$) δ ppm 1.14 (3 H, d, J = 6.3 Hz) 3.39 (1 H, ddd, J = 13.2, 7.4, 4.7 Hz) 3.68 (1 H, ddd, J = 13.2, 6.1, 4.2 Hz) 3.86-3.94 (1 H, m) 4.89 (1 H, d, J = 4.9 Hz) 7.88 (1 H, s) 7.89-7.95 (2 H, m) 8.20-8.25 (2 H, m) 8.39 (1 H, br s) 8.45 (1 H, t, J = 5.4 Hz) |
| 42 | — | ESI+; 492 |
| 43 | 42 | ESI+; 493 |
| 44 | 42 | ESI+; 495 |
| 45 | — | ESI+; 407 |
| 46 | — | ESI+; 457 |
| 47 | 46 | ESI+; 449 |
| 48 | 46 | ESI+; 447 |
| 49 | — | ESI+; 432 |
| 50 | 3 | ESI+; 364 |
| 51 | 3 | ESI+; 364 |
| 52 | 1 | APCI/ESI+; 312 |
| 53 | 1 | APCI/ESI+; 312 |
| 54 | 3 | ESI+; 442 |
| 55 | 3 | ESI+; 432 |
| 56 | 42 | API-ES+; 493 |
| 57 | 42 | ESI+; 493 |
| 58 | 42 | ESI+; 493 |
| 59 | 3 | ESI+; 342 |
| 60 | 3 | ESI+; 314 |
| 61 | 3 | ESI+; 408 |
| 62 | 3 | ESI+; 278 |
| 63 | — | ESI+; 382<br>$^1H$ NMR (500 MHz, DMSO-$d_6$) δ ppm 1.17-1.35 (4 H, m) 1.60-1.72 (2 H, m) 1.90-2.00 (4 H, m) 2.05-2.15 (4 H, m) 3.47-3.55 (1 H, m) 3.84-3.93 (1 H, m) 4.84 (1 H, br s) 5.69 (1 H, br s) 7.18-7.21 (1 H, m) 7.21-7.24 (1 H, m) 7.37 (1 H, d, J = 7.7 Hz) 10.33 (1 H, br s) |
| 64 | 3 | ESI+; 342 |
| 65 | 3 | ESI+; 308 |
| 66 | 3 | ESI+; 294 |
| 67 | 3 | ESI+; 370 |
| 68 | — | ESI+; 356<br>$^1H$ NMR (500 MHz, DMSO-$d_6$) δ ppm 1.16 (6 H, s) 1.99 (3 H, s) 2.11 (3 H, s) 3.49 (2 H, d, J = 5.7 Hz) 5.21 (1 H, s) 5.90 (1 H, t, J = 5.7 Hz) 7.18-7.21 (1 H, m) 7.21-7.24 (1 H, m) 7.37 (1 H, d, J = 7.5 Hz) 10.32 (1 H, s) |
| 69 | 3 | ESI+; 290 |
| 70 | — | ESI+; 342 |
| 71 | 3 | ESI+; 356 |
| 72 | 3 | ESI+; 382 |
| 73 | 3 | ESI+; 342 |
| 74 | 3 | ESI+; 397 |
| 75 | 3 | ESI+; 356 |
| 76 | — | ESI+; 356 |
| 77 | 3 | ESI+; 322, 324 |
| 78 | 3 | ESI+; 320, 322 |
| 79 | 3 | ESI+; 382 |
| 80 | — | ESI+; 382<br>$^1H$ NMR (500 MHz, DMSO-$d_6$) δ ppm 1.18-1.40 (3 H, m) 1.44-1.60 (1 H, m) 1.63-1.75 (2 H, m) 1.85-2.00 (2 H, m) 2.11-2.14 (3 H, m) 2.34 (3 H, s) 3.54-3.65 (1 H, m) 3.80-3.91 (1 H, m) 5.10 (1 H, br s) 7.26-7.34 (1 H, m) 7.36-7.41 (1 H, m) 7.48 (1 H, d, J = 7.7 Hz) 7.96 (1 H, br s) 11.06 (1 H, br s) 14.59 (1 H, br s)<br>2θ(°) = 14.5, 16.3, 17.2, 18.4, 18.9, 22.1, 23.6, 24.9, 25.7, 26.8 m.p.; 227.32° C. |

INDUSTRIAL APPLICABILITY

A compound of formula (I) or a salt thereof has an inhibitory action on NLRP3 inflammasome activation, and is expected to be usable as a prophylactic and/or therapeutic drug for an inflammatory disease and/or a neurodegenerative disease.

The invention claimed is:

1. A compound of formula (I) or a salt thereof:

[Formula 1]

(I)

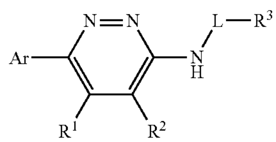

wherein

Ar is a group represented by the following formula (i) or (ii):

[Formula 2]

(i)

(ii)

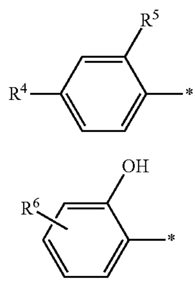

wherein * represents a bonding site to the pyridazine ring of formula (I);

L is $C_{1-6}$ alkylene or $C_{3-8}$ cycloalkylene;

$R^1$ is H, $C_{1-6}$ alkyl, $C_{3-8}$ cycloalkyl, aryl, cyano, —$OR^7$, —$N(C_{1-6}$ alkyl$)_2$, or heteroaryl optionally substituted with 1 to 4 $C_{1-6}$ alkyls;

$R^2$ is H, $C_{1-6}$ alkyl, $C_{3-8}$ cycloalkyl, aryl, cyano, —$OR^7$, —$N(C_{1-6}$ alkyl) 2, —C(═O)O—$C_{1-6}$ alkyl, —C(═O)$NR^8R^9$, or heteroaryl optionally substituted with 1 to 4 $C_{1-6}$ alkyls;

$R^3$ is OH, —NHC(═O) $R^{10}$ or —OC(═O)—$C_{1-6}$ alkyl;

$R^4$ is halogen, —O—$C_{1-6}$ alkyl or halogeno $C_{1-6}$ alkyl;

$R^5$ is H, $C_{3-8}$ cycloalkyl or halogeno $C_{1-6}$ alkyl;

$R^6$ is H, halogen, —O—$C_{1-6}$ alkyl or halogeno $C_{1-6}$ alkyl;

$R^7$ is-$C_{1-6}$ alkylene-O—$C_{1-6}$ alkylene-aryl or halogeno $C_{1-6}$ alkyl;

$R^8$ and $R^9$ are the same or different, and each are H or $C_{1-6}$ alkyl; or $R^8$ and $R^9$, together with a nitrogen atom to which $R^8$ and $R^9$ are bonded, form morpholine, piperazine or thiomorpholine, and the morpholine, piperazine or thiomorpholine is optionally substituted with $C_{1-6}$ alkyl; and $R^{10}$ is $C_{1-6}$ alkyl, halogeno $C_{1-6}$ alkyl or $C_{3-8}$ cycloalkyl, provided that when Ar is a group represented by formula (i) with $R^5$ being H, $R^4$ is halogeno $C_{1-6}$ alkyl, and one of $R^1$ and $R^2$ is a group other than H.

2. The compound or a salt thereof according to claim 1, wherein $R^5$ is $C_{3-8}$ cycloalkyl or halogeno $C_{1-6}$ alkyl.

3. The compound or a salt thereof according to claim 2, wherein $R^3$ is OH.

4. The compound or a salt thereof according to claim 3, wherein $R^1$ is H, $C_{1-6}$ alkyl or $C_{3-8}$ cycloalkyl, and $R^2$ is H, $C_{1-6}$ alkyl, $C_{3-8}$ cycloalkyl or cyano.

5. The compound or a salt thereof according to claim 4, wherein $R^1$ and $R^2$ are the same or different, and each are H or $C_{1-6}$ alkyl.

6. The compound or a salt thereof according to claim 5, wherein Ar is a group represented by formula (i).

7. The compound or a salt thereof according to claim 6, wherein each of $R^4$ and $R^5$ is halogeno $C_{1-6}$ alkyl.

8. The compound or a salt thereof according to claim 5, wherein Ar is a group represented by formula (ii).

9. The compound or a salt thereof according to claim 8, wherein $R^6$ is halogeno $C_{1-6}$ alkyl.

10. The compound or a salt thereof according to claim 1, wherein the compound is a compound selected from the following group of:

(2R)-1-({6-[2,4-bis(trifluoromethyl)phenyl]-4,5-dimethylpyridazin-3-yl}amino)propan-2-ol;

(2R)-1-({6-[2,4-bis(trifluoromethyl)phenyl]-5-methylpyridazin-3-yl}amino)propan-2-ol;

(2R)-1-({6-[2,4-bis(trifluoromethyl)phenyl]-4-methylpyridazin-3-yl}amino)propan-2-ol;

2-(6-{[(2R)-2-hydroxypropyl]amino}-4-methylpyridazin-3-yl)-5-(trifluoromethyl)phenol;

2-(6-{[(2R)-2-hydroxypropyl]amino}-5-methylpyridazin-3-yl)-5-(trifluoromethyl)phenol;

2-(6-{[(2R)-2-hydroxypropyl]amino}-4,5-dimethylpyridazin-3-yl)-5-(trifluoromethyl)phenol;

rac-(1R,2R)-2-({6-[2,4-bis(trifluoromethyl)phenyl]-5-methylpyridazin-3-yl}amino)cyclohexan-1-ol;

rac-(1R,2R)-2-({6-[2,4-bis(trifluoromethyl)phenyl]-4-methylpyridazin-3-yl}amino)cyclohexan-1-ol; and 2-(6-{[(1R,2R)-2-hydroxycyclohexyl]amino}-4,5-dimethylpyridazin-3-yl)-5-(trifluoromethyl)phenol.

11. A pharmaceutical composition comprising the compound or a salt thereof according to claim 1 and one or more pharmaceutically acceptable excipients.

12. A NLRP3 inflammasome activation inhibitor comprising the compound or a salt thereof according to claim 1.

13. A method of treating an inflammatory disease, comprising administering to a subject an effective amount of the compound of claim 1, or a salt thereof.

14. A method of treating a neurodegenerative disease, comprising administering to a subject an effective amount of the compound of claim 1, or a salt thereof.

15. A method of treating an inflammatory disease, comprising administering to a subject an effective amount of the pharmaceutical composition of claim 11.

16. A method of treating a neurodegenerative disease, comprising administering to a subject an effective amount of the pharmaceutical composition of claim 11.

* * * * *